US008557545B2

(12) United States Patent
Velders et al.

(10) Patent No.: US 8,557,545 B2
(45) Date of Patent: Oct. 15, 2013

(54) MODIFIED PHOSPHATASES

(75) Inventors: Markwin Paul Velders, Bilthoven (NL); Luigi Johannes Cornelius Jonk, Utrecht (NL); Willem Raaben, Amersfoort (NL); Marty Bernardus Fransiscus Wulferink, Ede (NL)

(73) Assignee: Am-Pharma B.V., Bunnik (NL)

( * ) Notice: Subject to any disclaimer, the term of this patent is extended or adjusted under 35 U.S.C. 154(b) by 363 days.

(21) Appl. No.: 12/451,137

(22) PCT Filed: Apr. 25, 2008

(86) PCT No.: PCT/NL2008/050249
§ 371 (c)(1),
(2), (4) Date: Dec. 31, 2009

(87) PCT Pub. No.: WO2008/133511
PCT Pub. Date: Nov. 6, 2008

(65) Prior Publication Data
US 2010/0143323 A1 Jun. 10, 2010

Related U.S. Application Data

(60) Provisional application No. 60/926,695, filed on Apr. 27, 2007.

(30) Foreign Application Priority Data

Apr. 27, 2007 (EP) .................................... 07107176

(51) Int. Cl.
C12P 19/34 (2006.01)
C12P 21/04 (2006.01)
(52) U.S. Cl.
USPC ...................................... 435/69.7; 435/91.53
(58) Field of Classification Search
None
See application file for complete search history.

(56) References Cited

U.S. PATENT DOCUMENTS

| | | |
|---|---|---|
| 6,290,952 B1 | 9/2001 | Poelstra et al. |
| 2007/0059300 A1 | 3/2007 | Kiss |
| 2009/0010912 A1 | 1/2009 | Brands et al. |
| 2010/0111923 A1 | 5/2010 | Pickkers et al. |
| 2011/0142817 A1 | 6/2011 | Brands et al. |

FOREIGN PATENT DOCUMENTS

| | | |
|---|---|---|
| JP | 4-349881 A | 12/1992 |
| JP | 9-98780 A | 4/1997 |
| JP | 2000-350596 A | 12/2000 |
| JP | 2005-65564 A | 3/2005 |
| WO | WO 2006/096527 A | 9/2006 |
| WO | WO 2008/133511 A2 | 11/2008 |

OTHER PUBLICATIONS

Le Du et al, Structural evidence of functional divergence in human alkaline phosphatases. J Biol Chem. Dec. 20, 2002;277(51):49808-14. Epub Oct. 7, 2002.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
NCBI Acc#NP_001622.2 versus Bossi et al. USPTO in house alignment Feb. 22, 2012.*
Bossi et al,Modifications in a flexible surface loop modulate the isozyme-specific properties of mammalian alkaline phosphatases. J Biol Chem. Dec. 5, 1993;268(34):25409-16.*
Millan et al, Alkaline Phosphatases : Structure, substrate specificity and functional relatedness to other members of a large superfamily of enzymes. Purinergic Signal. Jun. 2006;2(2):335-41. Epub Jun. 17, 2006.*
Berger et al, Cloning and sequencing of human intestinal alkaline phosphatase cDNA. Proc Natl Acad Sci U S A. Feb. 1987;84(3):695-8.*
Udenfriend et al, Prediction of omega site in nascent precursor of glycosylphosphatidylinositol protein. Methods Enzymol. 1995;250:571-82.*
Engle et al, Two rat intestinal alkaline phosphatase isoforms with different carboxyl-terminal peptides are both membrane-bound by a glycan phosphatidylinositol linkage. J Biol Chem. May 19, 1995;270(20):11935-40.*
Szuster-Ciesielska et al, The inhibitory effect of zinc on cadmium-induced cell apoptosis and reactive oxygen species (ROS) production in cell cultures. Toxicology. Apr. 14, 2000;145(2-3):159-71.*
Bennan et al., A Molecular Sensor System Based on Genetically Engineered Alkaline Phosphatase, Proceedings of the National Academy of Sciences of the United States of America, 1995, pp. 5783-5787, vol. 92, No. 13.
Beumer et al., Calf intestinal alkaline phosphatase, a novel therapeutic drug for lipopolysaccharide (LPS)-mediated diseases, attenuates LPS toxicity in mice and piglets, Journal of Pharmacology and Experimental Therapeutics, Nov. 2003, pp. 737-744, vol. 307, No. 2.
Millan, Jose Luis, Alkaline phosphatases: structure, substrate specificity and functional relatedness to other members of a large superfamily of enzymes, Purinergic Signalling, pp. 335-341, vol. 2.
Mornet et al., Structural evidence for a functional role of human tissue nonspecific alkaline phosphatase in bone mineralization, Journal of Biological Chemistry, Aug. 17, 2001, pp. 31171-31178, vol. 276. No. 33.
Naber et al., Serum alkaline phosphatase activity during zinc deficiency and long-term inflammatory stress. Clinica Chimica Acta, May 30, 1996, pp. 109-127, vol. 249, No. 1-2, Netherlands.
Sanchez et al., Induction of alkaline phosphatase in the inflamed intestine: a novel pharmacological target for inflammatory bowel disease, Biochemical Pharmacology, Dec. 15, 2004, pp. 2317-2326, vol. 68. No. 12, Pergamon, Oxford. GB.

(Continued)

Primary Examiner — Sheridan Swope
(74) Attorney, Agent, or Firm — Sterne, Kessler, Goldstein & Fox P.L.L.C.

(57) ABSTRACT

The invention relates to phosphatases and more in specific to (genetically) modified phosphatases, pharmaceutical compositions comprising (genetically) modified phosphatases and the use of (genetically) modified phosphatases for treating or curing for example sepsis, inflammatory bowel disease or other inflammatory diseases, or renal failure. The invention further relates to a method for producing phosphatases.

15 Claims, 11 Drawing Sheets

(56) References Cited

OTHER PUBLICATIONS

Tuin et al., Oral administration of alkaline phosphatase ameliorates colitis, Gastroenterology, Apr. 2007. p. A231, vol. 132, No. 4, Suppl. 2.

Van Veen et al., Alkaline phosphatase reduces hepatic and pulmonary injury in liver ischaemia—reperfusion combined with partial resection, The British Journal of Surgery APR 2006, Apr. 2006, pp. 448-456, vol. 93, No. 4.

Van Veen et al., Bovine intestinal alkaline phosphatase attenuates the inflammatory response in secondary peritonitis in mice, Infection and Immunity, Jul. 2005, pp. 4309-4314, vol. 73, No. 7.

Verweij et al., Protection against an *Escherichia coli*-induced sepsis by alkaline phosphatase in mice, Shock, Aug. 2004. pp. 174-179, vol. 22, No. 2.

Xu et al., Directed evolution of *E. coli* alkaline phosphatase towards higher catalytic activity, Biocatalysis and biotransformation 2003, 2003, pp. 41-47, vol. 21, No. 1, United Kingdom.

PCT International Search Report, PCT/NL2008/050249, dated Jan. 15, 2009.

U.S. Appl. No. 11/982,285, filed Oct. 31, 2007, van Ommen et al., Induction of Exon Skipping in Eukaryotic Cells.

U.S. Appl. No. 12/383,897, filed Mar. 30, 2009, van Ommen et al., Induction of Exon Skipping in Eukaryotic cells.

U.S. Appl. No. 10/395,031, filed Mar. 21, 2003, van Ommen et al., Induction of Exon Skipping in Eukaryotic Cells.

U.S. Appl. No. 11/233,507, filed Sep. 21, 2005, van Ommen et al., Modulation of Exon Recognition in Pre-MRNA by Interfering With the Secondary RNA Structure.

U.S. Appl. No. 11/233,495, filed Sep. 21, 2005, van Ommen et al., Modulation of Exon Recognition in Pre-MRNA by Interfering With Secondary RNA Structure.

U.S. Appl. No. 12/231,028, filed Aug. 27, 2008, Brouwer et al., Mutants of Lactoferrin.

U.S. Appl. No. 12/449,192, filed Jul. 27, 2009, Pickkers et al., The Use of Alkaline Phophatase in the Treatment of Reduced Renal Function.

Henthorn, P., et al., "Nucleotide and amino acid sequences of human intestinal alkaline phosphatase: Close Homology to placental alkaline phosphatase" *Proc. Natl. Acad. Sci. USA* 84:1234-1238 (1987).

Henthorn, P., et al., "Nucleotide and amino acid sequence of human intestinal alkaline phosphatase: Close homology to placental alkaline phosphatase" *Proc. Natl. Acad. Sci. USA* 84(12):4088 (1987).

Henthorn, P., et al., "Sequence and Characterization of the Human Intestinal Alkaline Phosphatase Gene" *The Journal of Biological Chemistry* 263: 12011-12019 (1988).

Kodama, H., et al., "Expression of a heterodimeric (placental-intestinal) hybrid alkaline phosphatase in KB cells" *Biochimica et Biophysics Acta* 1218:163-172 (1994).

Wray, L. et al., "Demonstration Using Monoclonal Antibodies of Inter-Locus Heteromeric Isozymes of Human Alkaline Phosphatase" *Journal of Immunological Methods*. 55:13-18 (1982).

Wang, E., et al., "Crystal Structure of Alkaline Phosphatase from the Antartic bacterium TAB5," *J. Mol. Biol. 366*: 1318-1331, Elsevier Ltd., England (2007).

Mandecki, W., et al., Patent Abstracts of Japan, English language Abstract of Japanese Patent Publication No. 04-349881, "Synthesized Alkaline Phosphatase Enzyme Having Improved Specific Activity," Japanese Patent Office, Patent & Utility Model Gazette DB (1992).

Boulain J., et al., Patent Abstracts of Japan, English language Abstract of Japanese Patent Publication No. 09-098780, "Modified Baterium Alkaline Phosphatase and its Use," Japanese Patent Office, Patent & Utility Model Gazette DB (1997).

Okamoto, M., et al., Patent Abstracts of Japan, English language Abstract of Japanese Patent Publicaiton No. 2000-350596, "Selective Assay of Secreted Alkaline Phosphatase Activity," Japanese Patent Office, Patent & Utility Model Gazette DB (2000).

Ueda, Hiroshi, Patent Abstract of Japan, English language Abstract of Japanese Patent Publication No. 2005-065564,"Sensor Protein," Japanese Patent Office, Patent & Utility Model Gazette DB (2005).

\* cited by examiner

Fig. 1

NP_001623 ALPP (Placental)

```
  1 IIPVEEENPDFWNREAAEALGAAKKLQPAQTAAKNLIIFLGDGMGVSTVTAARILKGQKK  60
 61 DKLGPEIPLAMDRFPYVALSKTYNVDKHVPDSGATATAYLCGVKGNFQTIGLSAAARFNQ 120
121 CNTTRGNEVISVMNRAKKAGKSVGVVTTTRVQHASPAGTYAHTVNRNWYSDADVPASARQ 180
181 EGCQDIATQLISNMDIDVILGGGRKYMFRMGTPDPEYPDDYSQGGTRLDGKNLVQEWLAK 240
241 RQGARYVWNRTELMQASLDPSVTHLMGLFEPGDMKYEIHRDSTLDPSLMEMTEAALRLLS 300
301 RNPRGFFLFVEGGRIDHGHHESRAYRALTETIMFDDAIERAGQLTSEEDTLSLVTADHSH 360
361 VFSFGGYPLRGSSIFGLAPGKARDRKAYTVLLYGNGPGYVLKDGARPDVTESESGSPEYR 420
421 QQSAVPLDEETHAGEDVAVFARGPQAHLVHGVQEQTFIAHVMAFAACLEPYTACDLAPPA 480
481 GTTDAAHPGRSVVPALLPLLAGTLLLLETATAP 513
```

AAI32679 ALPI (Intestinal)

```
  1 VIPAEEENPAFWNRQAAEALDAAKKLQPIQKVAKNLILFLGDGLGVPTVTATRILKGQKN  60
 61 GKLGPETPLAMDRFPYLALSKTYNVDRQVPDSAATATAYLCGVKANFQTIGLSAAARFNQ 120
121 CNTTRGNEVISVMNRAKQAGKSVGVVTTTRVQHASPAGTYAHTVNRNWYSDADMPASARQ 180
181 EGCQDIATQLISNMDIDVILGGGRKYMFPMGTPDPEYPADASQNGIRLDGKNLVQEWLAK 240
241 HQGAWYVWNRTELMQASLDQSVTHLMGLFEPGDTKYEIHRDPTLDPSLMEMTEAALRLLS 300
301 RNPRGFYLFVEGGRIDHGHHEGVAYQALTEAVMFDDAIERAGQLTSEEDTLTLVTADHSH 360
361 VFSFGGYTLRGSSIFGLAPSKAQDSKAYTSILYGNGPGYVFNSGVRPDVNESESGSPDYQ 420
421 QQAAVPLSSETHGGEDVAVFARGPQAHLVHGVQEQSFVAHVMAFAACLEPYTACDLAPPA 480
481 CTTDAAHPVAASLPLLAGTLLLLGASAAP 509
```

P10696 GCAP (Germ-cell or Placental-like)

```
  1 IIPVEEENPDFWNRQAAEALGAAKKLQPAQTAAKNLIIFLGDGMGVSTVTAARILKGQKK  60
 61 DKLGPETFLAMDRFPYVALSKTYSVDKHVPDSGATATAYLCGVKGNFQTIGLSAAARFNQ 120
121 CNTTRGNEVISVMNRAKKAGKSVGVVTTTRVQHASPAGAYAHTVNRNWYSDADVPASARQ 180
181 EGCQDIATQLISNMDIDVILGGGRKYMFPMGTPDPEYPDDYSQGGTRLDGKNLVQEWLAK 240
241 HQGARYVWNRTELLQASLDPSVTHLMGLFEPGDMKYEIHRDSTLDPSLMEMTEAALLLLS 300
301 RNPRGFFLFVEGGRIDHGHHESRAYRALTETIMFDDAIERAGQLTSEEDTLSLVTADHSH 360
361 VFSFGGYPLRGSSIFGLAPGKARDRKAYTVLLYGNGPGYVLKDGARPDVTESESGSPEYR 420
421 QQSAVPLDGETHAGEDVAVFARGPQAHLVHGVQEQTFIAHVMAFAACLEPYTACDLAPRA 480
481 GTTDAAHPGPSVVPALLPLLAGTLLLLGTATAP 513
```

AAI10910 (Tissue Non Specific)

```
  1 LVPEKEKDPKYWRDQAQETLKYALELQKLNTNVAKNVIMFLGDGMGVSTVTAARILKGQL  60
 61 HHNPGEETRLEMDKFPFVALSKTYNTNAQVPDSAGTATAYLCGVKANEGTVGVSAATERS 120
121 RCNTTQGNEVTSILRWAKDAGKSVGIVTTTRVNHATPSAAYAHSADRDWYSDNEMPPEAL 180
181 SQGCKDIAYQLMHNIRDIDVIMGGGRKYMYPKNKTDVEYESDEKARGTRLDGLDLVDTWK 240
241 SFKPRHKHSHFIWNRTELLTLDPHNVDYLLGLFEPGDMQYELNRNNVTDPSLSEMVVVAI 300
301 QILRKNPKGFFLLVEGGRIDHGHHEGKAKQALHEAVEMDRAIGQAGSLTSSEDTLTVVTA 360
361 DHSHVFTFGGYTPRGNSIFGLAPMLSDTDKKPFTAILYGNGPGYKVVGGERENVSMVDYA 420
421 HNNYQAQSAVPLRHETHGGEDVAVFSKGPMAHLLHGVHEQNYVPHVMAYAACIGANLGHC 480
481 APASSAGSLAAGPLLLALALYPLSVLF 507
```

Fig. 1 continued

Secretable ALPI with Crown-Domain of PLAP (chimera)

```
  1 VIPAEEENPAFWNRQAAEALDAAKKLQPIQKVAKNLILFLGDGLGVPTVTATRILKGQKN  60
 61 GKLGPETPLAMDRFPYLALSKTYNVDRQVPDSAATATAYLCGVKANFQTIGLSAAARFNQ 120
121 CNTTRGNEVISVMNRAKQAGKSVGVVTTTRVQHASPAGTYAHTVNRNWYSDADMPASARQ 180
181 EGCQDIATQLISNMDIDVILGGGRKYMFPMGTPDPEYPADASQNGIRLDGKNLVQEWLAK 240
241 HQGAWYVWNRTELMQASLDQSVTHLMGLFEPGDTKYEIHRDPTLDPSLMEMTEAALRLLS 300
301 RNPRGFYLFVEGGRIDHGHHEGVAYQALTEAVMFDDAIERAGQLTSEEDTLTLVTADHSH 360
361 VFSFGGYPLRGSSIFGLAPGKARDRKAYTVLLYGNGPGYVLKDGARPDVTESESGSPEYR 420
421 QQSAVPLDEETHGGEDVAVFARGPQAHLVHGVQEQSFVAHVMAFAACLEPYTACDI     480
481 CTTD 484
```

Secretable ALPP with Crown-Domain of ALPI (chimera)

```
  1 IIPVEEENPDFWNREAAEALGAAKKLQPAQTAAKNLIIFLGDGMGVSTVTAARILKGQKK  60
 61 DKLGPEIPLAMDRFPYVALSKTYNVDKHVPDSGATATAYLCGVKGNFQTIGLSAAARFNQ 120
121 CNTTRGNEVISVMNRAKKAGKSVGVVTTTRVQHASPAGTYAHTVNRNWYSDADVPASARQ 180
181 EGCQDIATQLISNMDIDVILGGGRKYMFRMGTPDPEYPDDYSQGGTRLDGKNLVQEWLAK 240
241 RQGARYVWNRTELMQASLDPSVTHLMGLFEPGDMKYEIHRDSTLDPSLMEMTEAALRLLS 300
301 RNPRGFFLFVEGGRIDHGHHESRAYRALTETIMFDDAIERAGQLTSEEDTLSLVTADHSH 360
361 VFSFGGYTLRGSSIFGLAPSKAQDSKAYTSILYGNGPGYVFNSGVRPDVNESESGSPDYQ 420
421 QQAAVPLSSETHAGEDVAVFARGPQAHLVHGVQEQTFIAHVMAFAACLEPYTACDLAPPA 480
481 GTTD 484
```

Fig. 6 – liver slice assay

Figure 9
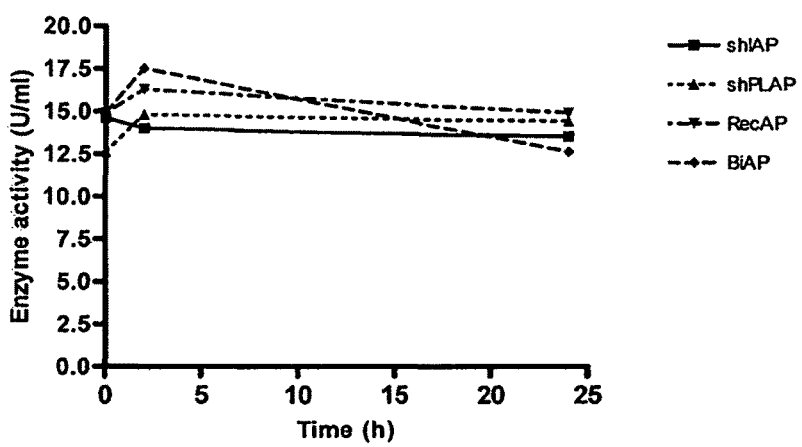
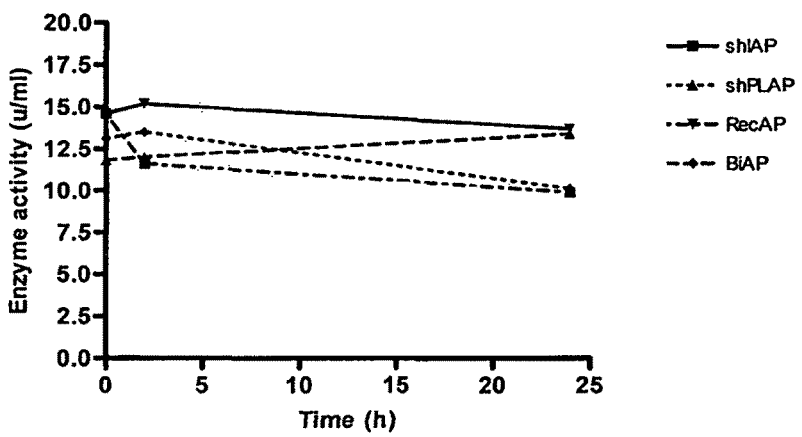
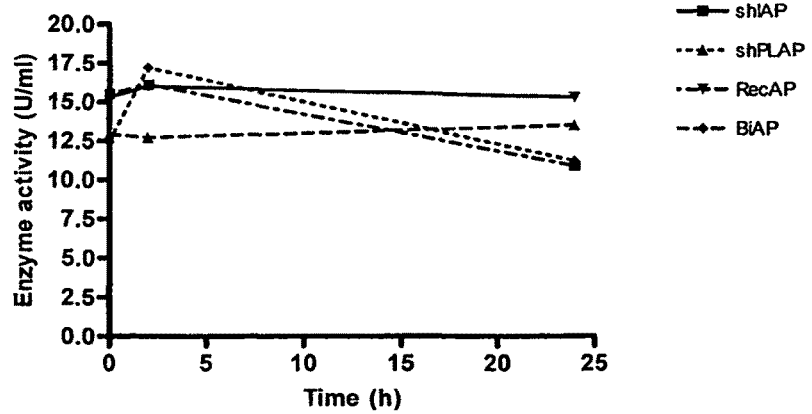

MODIFIED PHOSPHATASES

CROSS-REFERENCE TO RELATED APPLICATIONS

This application is the national stage entry of PCT International Application Number PCT/N:2008/050249, filed Apr. 25, 2008, designating the United States of America, and published in English as WO 2008/133511 A2 on Nov. 6, 2008, and claims priority under Article 8 of the Patent Cooperation Treaty to both European Patent Application EP 07107176.5, filed Apr. 27, 2007, and U.S. Ser. No. 60/926,695, filed Apr. 27, 2007.

BACKGROUND OF THE INVENTION

The invention relates to phosphatases and more in specific to (genetically) modified phosphatases, pharmaceutical compositions comprising (genetically) modified phosphatases and the use of (genetically) modified phosphatases for treating or curing for example sepsis, inflammatory bowel disease or other inflammatory disease, or renal failure. The invention further relates to a method for producing phosphatases.

A phosphatase is an enzyme that dephosphorylates its substrate; i.e. it hydrolyses phosphoric acid monoesters into a phosphate ion and a molecule with a free hydroxyl group. This action is directly opposite to that of phosphorylases and kinases, which attach phosphate groups to their substrates by using energetic molecules like ATP. Phosphatases can be categorised into two main categories: Cysteine-dependent Phosphatases (CDPs) and metallo-phosphatases. The latter ones are dependent on the presence of one or more metal ions in their active site(s) for activity.

CDPs catalyse the hydrolysis of a phosphoester bond via a phospho-cysteine intermediate. The free cysteine nucleophile forms a bond with the phosphorus atom of the phosphate moiety, and the P—O bond linking the phosphate group to the tyrosine is protonated, either by a suitably positioned acidic amino acid residue or a water molecule. The phospho-cysteine intermediate is then hydrolysed by another water molecule, thus regenerating the active site for another dephosphorylation reaction.

Metallo-phosphatases co-ordinate 1 or more catalytically essential metal ion(s) within their active site. There is currently some confusion of the identity of these metal ions, as successive attempts to identify them yield different answers. There is currently evidence that these metals could be Magnesium, Manganese, Iron, Zinc, or any combination thereof. It is thought that a hydroxyl ion bridging the two metal ions takes part in nucleophilic attack on the phosphate group Phosphatases act in opposition to kinases/phosphorylases, which add phosphate groups to proteins. The addition of a phosphate group may activate or de-activate an enzyme (e.g., Kinase signalling pathways) or enable a protein-protein interaction to occur (e.g., SH3 domains); therefore phosphatases are integral to many signal transduction pathways. It should be noted that phosphate addition and removal do not necessarily correspond to enzyme activation or inhibition, and that several enzymes have separate phosphorylation sites for activating or inhibiting functional regulation. CDK, for example, can be either activated or deactivated depending on the specific amino acid residue being phosphorylated. Phosphates are important in signal transduction because they regulate the proteins to which they are attached. To reverse the regulatory effect, the phosphate is removed. This occurs on its own by hydrolysis, or is mediated by protein phosphatases.

Without limiting the present invention, alkaline phosphatases are discussed in more detail as an example of the herein described and claimed phosphatases. Alkaline phosphatase (ALP) (EC 3.1.3.1) is a hydrolase enzyme responsible for removing phosphate groups from many types of molecules, including nucleotides, proteins, and alkaloids. The process of removing the phosphate group is called dephosphorylation. As the name suggests, alkaline phosphatases are most effective in an alkaline environment.

Alkaline phosphatase has become a useful tool in molecular biology laboratories, since DNA normally possesses phosphate groups on the 5' end. Removing these phosphates prevents the DNA from ligation (the 5' end attaching to the 3' end of the same or another molecule); also, removal of the phosphate groups allows radiolabeling (replacement by radioactive phosphate groups) in order to measure the presence of the labeled DNA through further steps in the process or experiment. For these purposes, the alkaline phosphatase from shrimp is the most useful, as it is the easiest to inactivate once it has done its job.

Another important use of alkaline phosphatase is as a label for enzyme immunoassays.

Moreover, alkaline phosphatases are used in the treatment of for example sepsis, inflammatory bowel disease, or renal failure.

Although the presently available (alkaline) phosphatases are useful in both diagnostics and disease treatment there is a need for alternative phosphatases with for example an altered (for example improved) specific activity, stability (for example in vivo $T_{1/2}$, or stability in respect of storage (shelf-life)) or substrate specificity. Moreover, there is also a need for phosphatases with a different pH or temperature or salt (in)dependency profile.

BRIEF SUMMARY OF THE INVENTION

The present invention provides alternative (genetically) modified phosphatases.

DESCRIPTION OF THE DRAWINGS

FIG. 1 Sequences of the four human alkaline phosphatase iso-enzymes. Note: these are the sequences of the mature proteins (i.e. without signal sequence) but before addition of the GPI-anchor and concomitant processing of the C-terminal amino acids with exception of the chimeric AP's (SEQ ID NOS: 1-6)

FIG. 4 At t=0 different recombinant alkaline phosphatases containing 450±50 Units were diluted 4000× in diluent buffer (0.025M glycine/NaOH pH 9.6/1 mM MgCl2/1% mannitol/0.05% BSA) with different concentrations of $Zn^{2+}$. Zn2+ significantly stabilized the specific activity of sALPI, whereas sALPP and the chimer catALPI/crownALPP retained their initial specific activity independent of the presence of Zn2+ in the medium. Specific activity of catALPI/ crownALPP is Zn independent FIG. 5 Show that in the absence of BSA and in the presence of Zn2+ depleting chelator EDTA, all isoforms lose their specific activity after 22 h. Specific activity of ALPI but not catALPI/crownALPP decreases in time FIG. 6 Shows that in the presence of different recombinant human alkaline phosphatases (sALPI, sALPP, GPI-anchored ALPI, catALPI/crownALPP) at different concentrations, the NOx production was significantly inhibited. Bovine derived ALPI was used as a positive control and solvent as a negative control. LPS-induced NOx production by liver slices is inhibited by different secretable isoforms of human alkaline phosphatase FIG. 7 Relative enzyme activities of different secretable human recombinant alkaline phosphatases and bovine intestinal phosphatase (BIAP) stored for 24 h in 01.M buffers of different pH values.

DETAILED DESCRIPTION OF THE INVENTION

Figure 2:
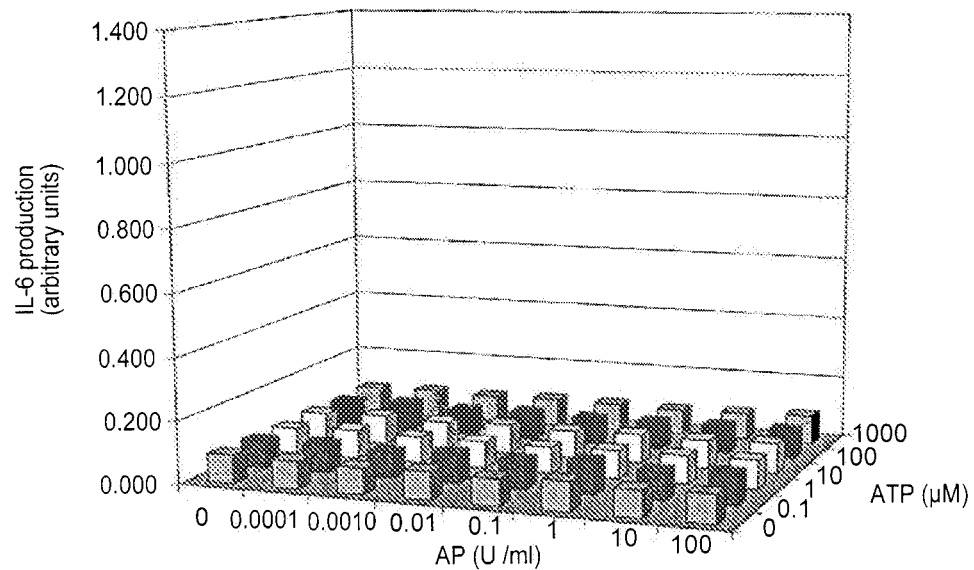
FIG. 2 4×105 T84 cells were plated into 12 well plates and cells were incubated with without 1 μg/mlLPS for 2 hours in the presence or absence of different concentrations of ATP and/or AP. ATP alone is not sufficient to stimulate production of IL-6 in RAW cells upon incubation with T84 supernatant. No effect on IL-6 production is seen upon addition of AP FIG. 3 4×10$^5$ T84 cells were plated into 12 well plates and cells were incubated with 1 μg/ml LPS for 2 hours in the presence or absence of different concentrations of ATP and/or AP. Increasing ATP concentrations amplify the LPS-induced IL-6 production in RAW cells upon incubation with T84 supernatant. Alkaline phosphatase inhibits the amplifying effect of ATP but not the LPS-induced IL-6 production itself.

In a first embodiment, the invention provides an isolated or recombinant alkaline phosphatase comprising a crown domain and a catalytic domain, wherein said crown domain and said catalytic domain are obtained from different alkaline phosphatases. These mutants are herein further referred to as "domain swapped mutants".

Alkaline phosphatase (AP); EC 3.1.3.1 according to IUBMB Enzyme Nomenclature, the common name is alkaline phosphatase (AP), is an enzyme that catalyzes the reaction of a phosphatase monoester and $H_2O$ to an alcohol and phosphate. Other name(s) for AP are alkaline phosphomonoesterase; phosphomonoesterase; glycerophosphatase; alkaline phosphohydrolase; alkaline phenyl phosphatase; orthophosphoric-monoester phosphohydrolase (alkaline optimum). The systemic name of AP is phosphate-monoester phosphohydrolase (alkaline optimum).

AP is a wide specificity enzyme, it also catalyses transphosphorylations. In humans and other mammals at least four distinct, but related alkaline phosphatases are known. In humans these are intestinal, placental, placental-like, and liver/bone/kidney (or tissue non-specific) alkaline phosphatase. The first three are located together on chromosome 2 while the tissue non-specific form is located on chromosome 1. The exact physiological functions of the APs are not known, but AP appears to be involved in a large number of physiological processes.

The placental alkaline phosphatase is herein abbreviated as ALPP or PLAP. The abbreviations ALPI or IAP refer to intestinal alkaline phosphatase. The placental-like 2 alkaline phosphatase is herein abbreviated as ALPP2, ALPG or GCAP and the abbreviations ALPL, TNSALP, TNAP or BLK are herein used to refer to liver/tissue non-specific alkaline phosphatase. The different abbreviations for one and the same alkaline phosphatase are used interchangeably herein.

From a conformational point of view, an alkaline phosphatase roughly consists of two domains: a crown domain and an active-site domain. The active-site domain can be divided in separate parts like the catalytic residue and the three metal ion sites (Zn1, Zn2 and Mg3). From a primary structure point of view it is clear that the crown domain is flanked by the amino acids that form the active site domain. Hence, in a preferred embodiment, the catalytic domain is not composed of a contiguous sequence of amino acids, but is flanking the crown domain.

The amino acid sequence of alkaline phosphatases and the relative positions of the catalytic and crown domain are known by the skilled person. As an example, reference is made to FIG. 1 which shows, amongst others, the amino acid sequence of the four human alkaline phosphatases. The crown domain is underlined in these sequences. The domain swapped mutants of the invention preferably have been made by replacing their own crown domain (as underlined) by a crown domain of another phosphatase (as underlined). For example, the crown domain of ALPP is located between amino acids 366 to 430 and hence in a preferred embodiment reference to the crown domain corresponds to the amino acids 366 to 430 in FIG. 1, i.e. in a preferred embodiment the invention provides an isolated or recombinant alkaline phosphatase comprising a crown domain and a catalytic domain, wherein said crown domain and said catalytic domain are obtained from different alkaline phosphatases and which crown domain in the ALPP of FIG. 1 is located between amino acid 366 to 430.

Alkaline phosphatases are present in virtually all organisms from bacteria to humans. In a preferred embodiment, the invention provides an isolated or recombinant alkaline phosphatase comprising a crown domain and a catalytic domain, wherein said crown domain and said catalytic domain are obtained from different alkaline phosphatases and wherein at least one of said different phosphatases is a human phosphatase. The other phosphatase is for example ECAP (*Escherichia coli* alkaline phosphatase) or one of the seven known BIAPs (Bovine Intestinal Alkaline Phosphatase). In a preferred embodiment, the invention provides an isolated or recombinant alkaline phosphatase comprising a crown domain and a catalytic domain, wherein said crown domain and said catalytic domain are obtained from different alkaline phosphatases and wherein the different alkaline phosphatases are human phosphatases. This is especially useful if the modified phosphatase is subsequently used in human therapy, for example in the treatment of sepsis, inflammatory bowel disease or other inflammatory disease, or renal failure. It is expected that such (genetically) modified phosphatases of human origin are not or very little immunogenic. However it is clear to the skilled person that if a modified phosphatase is for example used in "in vitro" or "ex vivo" diagnostics a modified phosphatase may well be composed of for example a human and an *E. coli* alkaline phosphatase or may be composed of a bovine and an *E. coli* alkaline phosphatase.

In yet another preferred embodiment, the invention provides an isolated or recombinant alkaline phosphatase comprising a crown domain and a catalytic domain, wherein said crown domain and said catalytic domain are obtained from different alkaline phosphatases and wherein said crown domain is the crown domain of ALPP and wherein said catalytic domain is the catalytic domain of ALPI. Preferably, at least one of said different phosphatases is a human phosphatase and in an even more preferred embodiment, both different phosphatases are human phosphatases.

Until the present invention it was generally believed that the catalytic domain of an alkaline phosphatase was the most important domain in respect of specific activity. Moreover, it was believed that the crown domain was involved in the stability of an alkaline phosphatase. Thus, upon testing a recombinant alkaline phosphatase comprising the catalytic domain of ALPI and the crown domain of ALPP (further referred to as catALPi/crownALPP) it was expected that the activity of this recombinant alkaline phosphatase would be comparable to the activity of ALPI. However, production of catALPI/crownALPP in a medium with no or very little $Zn^{2+}$, for example Freestyle™ 293 expression medium (GIBCO), resulted in a specific activity of approximately 600 U/mg whereas ALPI produced by the same cell line and in the same medium resulted in a specific activity of about 30 U/mg.

Even more surprisingly was the effect of adding $Zn^{2+}$ ions to the growth medium of the producer cells: this has little effect on the specific activity of catALPI/crownALPP whereas the specific activity of ALPI increased to approximately 750 U/mg. Addition of similar concentrations of $Zn^{2+}$ after production induced only a 2-fold increase in specific activity of ALPI after 16 h.

A summary of these results is provided in Tables 1 and 2.

Without being bound by theory, it is thought that the crown domain of ALPP provides a conformational change in the produced recombinant catALPI/crownALPP which results in a higher specific activity and a $Zn^{2+}$ independent enzyme, i.e. the presence of the crown domain of ALPP results in relative high specific activity and is considered to be $Zn^{2+}$ independent.

Furthermore, it was not only shown that ALPI required high $Zn^{2+}$ concentrations during production to increase the specific activity of the enzyme, but also that specific activity of ALPI decreased within 24 hours in $Zn^{2+}$ deficient medium, whereas catALPI/crownALPP retained its initial specific activity under the same conditions. These results imply that the in vivo activity is $Zn^{2+}$ independent. Such an enzyme whose activity is independent of $Zn^{2+}$ could be useful in illnesses where $Zn^{2+}$ depletion is part of the pathology (e.g. nutritional defects, alcohol abuse and intestinal integrity damage, chronic infections including sepsis, or inflammatory diseases in general) or where addition of $Zn^{2+}$ may be contraindicated (e.g. acute phase of sepsis, autoimmune diseases). Apart from production and application advantages, catALPI/crownALPP also has advantages in respect to stability during storage.

It has thus been shown that native AP, such as ALPI, loses its enzymatic activity in environments with low $Zn^{2+}$ concentrations. Thus in diseases, wherein $Zn^{2+}$ depletion is part of the pathology, said native AP is unable to unfold its enzymatic activity at the site where it is thought to be the most beneficial, e.g. at the site of inflammation. In contrast, a recombinant AP not susceptible to low $Zn^{2+}$ concentrations, e.g. catALPI/crownALPP retains its activity in an environment with low Zn2+ concentration, e.g. at an inflammation site. In a healthy individual $Zn^{2+}$ serum reference values are between 10 and 20 μM. For instance in alcohol abuse or during malnutrition, these levels can decrease to less than 10 μM or even less than 1 μM. Several enzymes in the human body depend on $Zn^{2+}$ for their activity and for instance immunologic responses are more effective if sufficient levels of $Zn^{2+}$ are present. The innate as well as the specific parts of the immune system are known to be influenced by zinc and it has been established that zinc containing proteins accumulate at sites of inflammation. Furthermore, (sub)chronic inflammation, such as rheumatoid arthritis, sepsis, and Crohn's disease present with serum zinc deficiency. Surprisingly, the invention also provides the insight that catALPI/crownALPP retains its activity in much broader pH range than unmodified (recombinant) alkaline phosphatase. Given the fact that many disorders, such as inflammation and/or ischemia, encompass disturbances in tissue pH, catALPI/crownALPP is thus particularly useful for the treatment of such diseases. In one embodiment therefore, the invention provides a use of a phosphatase comprising a catalytic domain of ALPI and a crown domain of ALPP as a medicament, preferably for use in treating a disease which is accompanied by disturbed tissue pH, preferably said disease comprises an inflammatory disease and/or a disease accompanied with ischemia.

The invention provides the insight that a recombinant phosphatase comprising the catalytic domain of ALPI and the drown domain of ALPP (catALPI/crownALPP) is especially useful in the treatment of a disease that is accompanied with local or systemic $Zn^{2+}$ deficiency. In another embodiment therefore, the invention provides a use of a phosphatase comprising a catalytic domain of ALPI and a crown domain of ALPP as a medicament, preferably for use in treating a disease which is accompanied by $Zn^{2+}$ deficiency Preferably said disease comprises an inflammatory disease, more preferably selected from the group consisting of autoimmune diseases, rheumatoid arthritis, asthma, chronic obstructive pulmonary disease, atherosclerosis, inflammatory bowel disease, sepsis, neurodermitis and diseases depicted in Table 10.

In another embodiment, the invention provides the use of a phosphatase comprising a catalytic domain of ALPI and a crown domain of ALPP in the preparation of a medicament for the treatment of a disease which is accompanied by $Zn^{2+}$ deficiency, preferably said disease comprises an inflammatory disease, more preferably a disease selected from the group consisting of autoimmune diseases, rheumatoid arthritis, asthma, chronic obstructive pulmonary disease, atherosclerosis, inflammatory bowel disease, sepsis, neurodermitis and diseases depicted in Table 10.

In yet another embodiment, the invention provides a method for treating a subject (preferably a human) to treat a disease which is accompanied by $Zn^{2+}$ deficiency, comprising administering an effective amount of a phosphatase comprising a catalytic domain of ALPI and a crown domain of ALPP to a subject in need thereof, wherein said disease preferably comprises an inflammatory disease, more preferably selected from the group consisting of autoimmune diseases, rheumatoid arthritis, asthma, chronic obstructive pulmonary disease, atherosclerosis, inflammatory bowel disease, sepsis, neurodermitis and diseases depicted in Table 10.

In another preferred embodiment, the invention provides an isolated or recombinant alkaline phosphatase comprising a crown domain and a catalytic domain, wherein said crown domain and said catalytic domain are obtained from different alkaline phosphatases and wherein said crown domain is the crown domain of ALPI and wherein said catalytic domain is the catalytic domain of ALPP (further referred to as catALPP/crownALPI). Preferably, at least one of said different phosphatases is a human phosphatase and in an even more preferred embodiment, both different phosphatases are human phosphatases.

Other preferred domain swapped mutants that are based on the human alkaline phosphatases are:

| Catalytic domain | Crown domain | Referred to as |
|---|---|---|
| ALPI | GCAP | catALPI/crownGCAP |
|  | TNAP | catALPI/crownTNAP |
| ALPP | GCAP | catALPP/crownGCAP |
|  | TNAP | catALPP/crownTNAP |
| GCAP | ALPI | catGCAP/crownALPI |
|  | ALPP | catGCAP/crownALPP |
|  | TNAP | catGCAP/crownTNAP |
| TNAP | ALPI | catTNAP/crownALPI |
|  | ALPP | catTNAP/crownALPP |
|  | GCAP | catTNAP/crownGCAP |

For the sake of clarity, ALPI is intestinal AP, ALPP is placental AP, GCAP is placental-like AP and TNAP is tissue non-specific AP.

It is clear that also combinations between the catalytic domain of ECAP or any of the human forms (ALPI, ALPP, GCAP or TNAP) with the crown domain of BIAP can be made. Moreover, combinations of the crown domain of BIAP with the catalytic domain of ECAP or any of the human forms can also be produced.

Throughout the specification, examples and literature in the art, other nomenclature is used to designate the respective isoforms of alkaline phosphatase. For the sake of clarity, in the table below the names and abbreviations commonly used, or used in this application is listed.

| ALKALINE PHOSPHATASES | ABBREVIATIONS |
|---|---|
| Placental alkaline phosphatase | ALPP, PLAP, |
| Secretable Placental alkaline phosphatase | shPLAP, sALPP |
| Intestinal alkaline phosphatase | ALPI, IAP hIAP |
| Secretable Intestinal alkaline phosphatase | shIAP, sALPI |
| Placental-like alkaline phosphatase | GCAP |
| Tissue non specific alkaline phosphatase | TNAP, BLK, ALPL, TNSALP |
| E. coli alkaline phosphatase | ECAP |
| Bovine intestinal alkaline phosphatase | BIAP |
| Recombinant alkaline phosphatase comprising the catalytic domain of ALPI and the crown domain of ALPP | catALPI/crownALPP, RecAP, Xinplap |
| Recombinant alkaline phosphatase comprising the catalytic domain of ALPI and the crown domain of ALPP | catALPI/crownALPI, shPLAP-hIAP-CD |

Another class of useful modified phosphatases are phosphatases which under natural conditions are linked to the membrane of a cell via a glycosylphosphatidylinositol (GPI) anchor but which are now modified such that they are no longer attached to the membrane of a cell. Examples of phosphatases that are GPI-anchored are alkaline phosphatase and 5'-nucleotidase. All isoenzymes are functionally active in the cell membrane and GPI-anchor deficient forms are not naturally present at detectable levels. Although serum alkaline phosphate activity has been demonstrated it is generally accepted that the enzyme is still present in shed membrane fractions or membrane vesicles. AP activity in milk is also present in fractions containing membrane vesicles. The GPI anchor is stored as a precursor molecule in the cell where it is attached to the attachment site through a transamidase. The backbone of the GPI-anchor is identical in mammals, but cell-type dependent modifications are known.

Alkaline phosphatases are predominantly found in association with plasma-membranes via their GPI anchor. For example, neutrophils present the enzyme against the background of their negatively charged cell membrane instead of releasing it into the inflammatory microenvironment. For this reason it is commonly accepted that for optimal in vivo activity of AP the enzyme should be embedded in a cell membrane or a vesicular membrane. Furthermore it has been observed that poly-anionic substrates can further contribute to favourable anionic conditions in vivo for phosphatase activity of phosphatase enzymes and derivatives thereof normally having an optimum at an alkaline pH, in particular for phosphatase activity of alkaline phosphatase.

For pharmaceutical use of AP in human subjects it is for most applications a requirement to apply human forms of the enzyme for medicaments and treatment, as AP forms obtained from other species may be immunogenic in human subjects and treatment could elicit immunological reactions and pathological side effects. In some subjects even lethal side effects i.e. anaphylactic shock (shown in our animal studies) may occur and the risks of immunological side effects should therefore be minimized. As isolation of AP from humans is practically not feasible, human recombinant forms of the AP proteins can be routinely produced in different recombinant expression platforms. However, expression and purification of GPI containing and membrane-anchored proteins is notoriously difficult; GPI proteins are difficult to separate from membranes and difficult to isolate and purify. However, the GPI anchor and membrane localisation have always been regarded as essential for the biological activity of AP.

This part of the current invention is based on the surprising finding that human AP enzymes lacking a GPI-anchor and which enzymes are thus soluble and easily secreted by recombinant protein expression systems, display significant phosphatase activity at physiological pH levels towards biologically relevant phosphorylated substrates in a liver-cell based biologic assay.

In one of the embodiments, the invention provides an isolated or recombinant phosphatase comprising a modification in the glycosylphosphatidylinositol (GPI) signal sequence, wherein said modification results in a secreted phosphatase, i.e. the phosphatase is not attached to the cell membrane.

In a preferred embodiment, the invention provides an isolated or recombinant phosphatase comprising a modification in the glycosylphosphatidylinositol (GPI) signal sequence, wherein said modification results in a secreted phosphatase that is biological active, i.e. it show activity towards a biological (relevant) substrate.

There is no general sequence responsible for the attachment of a GPI anchor, but there is a clear consensus:
1) hydrophobic stretch of amino acids at the C-terminus (at least 11 amino acids, but preferably more than 11 amino acids)
2) Upstream of the hydrophobic region, a spacer of hydrophylic amino acids (5-12 amino acids)
3) GPI is attached to a small amino acid: glycine, aspartic acid, asparagine, alanine, serine or cysteine.
4) The 2 subsequent amino acids downstream of the GPI attachment site must be small amino acids and in the majority of cases they are selected from glycine, aspartic acid, asparagine, alanine, serine or cysteine.

Based on this consensus, the skilled person is capable of mutating this consensus, for example by inserting one or multiple amino acids and disrupting part of the consensus. However in a preferred embodiment, the invention provides an isolated or recombinant phosphatase comprising a modification in the glycosylphosphatidylinositol (GPI) signal sequence, wherein said modification results in a secreted phosphatase and wherein said modification comprises a mutation or a deletion of the amino acid sequence encompassing the consensus GPI signal sequence.

For applications in human therapy it is desired that the resultant modified phosphatase is not or very little immunogenic, i.e. that the modified phosphatase is essentially of human origin. In a preferred embodiment, the invention provides an isolated or recombinant phosphatase comprising a modification in the glycosylphosphatidylinositol (GPI) signal sequence, wherein said modification results in a secreted phosphatase (preferably with activity against a biological relevant substrate) and wherein said phosphatase is a human phosphatase.

Examples of phosphatases that are GPI-anchored are alkaline phosphatase and 5'-nucleotidase and hence in a preferred embodiment, the invention provides an isolated or recombinant phosphatase comprising a modification in the glycosylphosphatidylinositol (GPI) signal sequence, wherein said modification results in a secreted phosphatase and wherein said phosphatase is an alkaline phosphatase for example a human alkaline phosphatase, such as human liver-kidney-bone phosphatase, human intestinal alkaline phosphatase, or human placental-like alkaline phosphatase.

It is clear that any of the described secretable modified phosphatase can for example be produced by introducing into a host cell a nucleic acid capable of encoding said secretable phosphatase in operable linkage with regulatory sequences and allowing said host cell to express said secretable phosphatase and optionally isolating the produced phosphatase from the medium in which the host cell are grown and/or maintained. However, apart from mutations in the above mentioned GPI-attachment sequence, other methods exist that make GPI-anchorless, secreted proteins:

1) After expression as membrane anchored proteins, phospholipases may be used to cleave off the GPI anchor. Hence the invention also provides a method for producing a secreted phosphatase comprising culturing a host capable of expressing a membrane anchored phosphatase, allowing said host cell to produce said phosphatase and incubating the obtained cells with a phospholipase and optionally isolating the released phosphatase. The membrane anchored phosphatase is for example a wild type (or natural or non-modified) phosphatase. However, the membrane anchored phosphatase can comprise mutations in other parts of its sequence (for example the crown domain).

2) Interference with the production of the GPI anchor or the use of a cell (type) that is deficient in GPI anchor production may also be used to make a secretable form of an otherwise GPI-anchored protein. Examples of cell lines that have been made to be deficient in GPI anchoring biochemistry are e.g. Jurkat, AM-B, C84, BW, S49, CHO and Raji. In yet another embodiment the invention therefore provides a method for producing a secreted phosphatase comprising culturing a host cell capable of expressing a secretable (alkaline) phosphatase (for example a host cell comprising a nucleic acid sequence encoding any of the mentioned modified secreted (alkaline) phosphatases), allowing said host to produce said secretable phosphatase and optionally isolating the produced phosphatase, wherein said host cell is not capable of biosynthesis of functional GPI anchored proteins. However, the host cell may also produce a phosphatase with a functional GPI signal sequence.

3) interference with or the use of a cell deficient in transamidases may be used to inhibit attachment of a GPI anchor to the protein, rendering the protein anchorless and secretable. Such a deficient cell has been obtained through mutagenesis in CHO.

It is clear to the skilled person that a modified phosphatase which comprises a crown domain and a catalytic domain, wherein said crown domain and said catalytic domain are obtained from different alkaline phosphatases can be further modified and made secretable. Hence, in a preferred embodiment, the invention provides an isolated or recombinant phosphatase comprising a modification in the glycosylphosphatidylinositol (GPI) signal sequence, wherein said modification results in a secreted phosphatase and wherein said recombinant phosphatase further comprises a crown domain and a catalytic domain that are obtained from different phosphatases. Examples of such (alkaline) phosphatase mutants are provided in FIG. 1. Such a combined or "double" mutant results for example in a modified phosphatase with a certain specific activity, stability or substrate specificity and at the same time production of such a product is greatly enhanced by the fact that it can be isolated from the medium surrounding the producer cells.

The catalytic domain of alkaline phosphatases is composed of several amino acid sequences that are not contiguous in the primary sequence of the enzyme. The catalytic domain contains the catalytic Serine residue (Ser92 in ALPP) that serves as an acceptor for the phosphate group that is cleaved off the substrate in the dephosphorylation reaction. The catalytic domain of the enzyme further contains one or more metal ions. Specific amino acid residues contained within the catalytic domain are responsible for the binding and coordination of the metal ions that are involved in the dephosphorylation reaction. In ALPP the metal coordinating residues are: Asp42, His153, Ser155, Glu311, Asp316, His320, Asp357, His358, His360 and His 432.

In yet another embodiment, the invention provides an isolated or recombinant phosphatase comprising a mutation in the vicinity of a catalytic residue and/or in a metal ion-coordinating phosphate-binding pocket. The skilled person is very well capable of identifying and mutating amino acids around (i.e. in the, preferably conformational, vicinity of) a catalytic residue and/or in a metal ion-coordinating phosphate pocket. As already has been described above, sequences of phosphatases are known. As an example, FIG. 1 shows, amongst others the amino acid sequence of four human alkaline phosphatases.

In a preferred embodiment, the invention provides an isolated or recombinant phosphatase comprising a mutation in the vicinity of a catalytic residue and/or in a metal ion-coordinating phosphate-binding pocket wherein said phosphatase is a human phosphatase. This is especially useful if the modified phosphatase is subsequently used in human therapy, for example in the treatment of sepsis, inflammatory bowel disease or other inflammatory disease, or renal failure. It is expected that such (genetically) modified phosphatases of human origin are not or very little immunogenic. However it is clear to the skilled person that if a modified phosphatase is for example used in "in vitro" or "ex vivo" diagnostics a modified phosphatase may well be composed of for example a human and an *E. coli* alkaline phosphatase or may be composed of a bovine and an *E. coli* alkaline phosphatase.

In yet another preferred embodiment, said phosphatase is an alkaline phosphatase.

The metal ion-coordinating phosphate-binding pocket is, at least for the human alkaline phosphatase isoforms, conserved. It consists of two Zn binding stretches and one Mg binding stretch that contain the amino acids Asp316, His320 and His432 for Zn1, Asp42, Asp 357 and Asp358 for Zn2 and Ser155 and Glu31 for Mg, respectively (reference is made to ALPP FIG. 1)

Mutations of the coordinating amino acid residues and/or residues located in the vicinity of the coordinating residues are likely to affect the catalytic properties of the resulting mutant enzyme in a positive or negative manner. For example, in ALPP amino acid residues 44, 87, 93, 322, 323 and 429 are located in the vicinity of the of the coordinating residues. Mutagenesis of these residues by substitution with one, two, three or four of the corresponding amino acids of ALPI may affect the catalytic properties of the enzyme. Vice versa, substitution of amino acid residues 44, 87, 93, 322, 323 and 429 of ALPI with the corresponding amino acids of ALPP may affect the catalytic properties of the ALPI enzyme. Tables 4 and 5 show (combinations of) the amino acids that may be substituted.

Hence, in a preferred embodiment, the invention provides an isolated or recombinant phosphatase comprising a mutation in the vicinity of a catalytic residue and/or in a metal ion-coordinating phosphate-binding pocket, wherein said mutation is a mutation as depicted in Table 4, 5 or 6.

It is clear to the skilled person that an isolated or recombinant phosphatase comprising a mutation in the vicinity of a catalytic residue and/or in a metal ion-containing phosphate-binding pocket can be further modified to for example comprise a modification in the GPI signal sequence. Such a mutant can even be further modified by domain of the catalytic and crown domain, i.e. such that said crown domain and catalytic domain that are obtained from different phosphatases.

In yet another embodiment, an isolated or recombinant phosphatase comprising a mutation in the vicinity of a catalytic residue and/or in a metal ion-coordinating containing phosphate-binding pocket can also be further modified by domain swapping of the catalytic and crown domain, i.e. such that said crown domain and catalytic domain that are obtained from different phosphatases.

Moreover, in yet another embodiment the invention provides an isolated or recombinant phosphatase comprising a mutation in the vicinity of a catalytic residue and/or in a metal ion-coordinating phosphate-binding pocket.

Molecular biology techniques to arrive at any of the described (genetically) modified phosphatases are well known by the skilled person and include techniques such as restriction enzyme incubations, ligations, PCR, introduction of mutations etc.

In yet another embodiment, the invention provide a nucleic acid sequence encoding a phosphatase as described herein, for example a nucleic acid sequence encoding a domain swapped mutant or a nucleic acid encoding a secreted phosphatase or a nucleic acid sequence encoding a secreted domain swapped mutant etc. The invention further provides a vector comprising a nucleic acid sequence encoding a phosphatase as described herein. Such a vector preferably comprises additional nucleic acid sequences such as elements necessary for transcription/translation of the nucleic acid sequence encoding a phosphatase (for example promoter and/or terminator sequences). Said vector may also comprise nucleic acid sequences coding for selection markers (for example an antibiotic) to select or maintain host cells transformed with said vector. Examples of suitable vectors are cloning or expression vectors. Any vector suitable for mediating expression in a suitable host cell may be used according to the invention, either integrated or episomally replicating in a host cell. The vector may be a plasmid, a virus (comprising a retrovirus, adenovirus, adeno-associated virus, baculovirus), cosmid, a phage or a phagemid, an episomal vector or an artificial chromosome.

Furthermore the invention also provides a host cell comprising a nucleic acid sequence or vector as described. The cell may be a eukaryotic cell, preferably a mammalian cell, a plant cell or a yeast cell, that is suitable for production of recombinant proteins. Suitable yeast host cells comprise *Saccharomyces cerevisiae* and *Pichia pastoris*. Preferred Lost cells are mammalian (or more preferred human) derived cells such as BHK, HEK293, CHO or PerC6™.

A nucleic acid sequence encoding a phosphatase as described herein or a vector comprising said nucleic acid sequence or a host cell comprising said nucleic acid sequence or a vector comprising said nucleic acid sequence are very useful in the production of modified phosphatases. Phosphatases comprise glycosylation sites and hence the phosphatases are preferably produced in cells that provide the desired glycosylation pattern. In a preferred embodiment, the used production system is a mammalian (for example human) in vitro production platform and even more preferably the production involves large-scale production. In another preferred embodiment, the used production system is a plant or yeast or mammalian (preferably non-human) platform in which an artificial human-like glycosylation pattern is introduced.

Upon testing different production methods, the inventors of the present invention surprisingly determined that the presence of $Zn^{2+}$ ions during the production of a wild type or mutant (alkaline) phosphatase can have an impact on the specific activity of the produced phosphatase. For example, the specific activity of ALPI can be increased from 30 U/mg to 750 U/mg by adding $Zn^{2+}$ to the growth medium of the used host cell. Medium normally used for culturing host cells comprises 0.5-3 nM $Zn^{2+}$. Upon the addition of $Zn^{2+}$ up to 1 mM the specific activity drastically improved. It is therefore concluded that ALPI is a $Zn^{2+}$ dependent phosphatase. This is in contrast to the already described catALPI/crownALPP mutant that seems to be independent of $Zn^{2+}$, i.e. the absence of $Zn^{2+}$ during the culturing of the host cells does not significantly influence the specific activity of the produced phosphatase nor does the absence of $Zn^{2+}$ during storage and during the reaction decrease specific activity.

In yet another embodiment, the invention provides a method for producing a phosphatase comprising culturing a host cell capable of expressing said phosphatase in a medium comprising $Zn^{2+}$ and allowing the cell to produce said phosphatase. In a preferred embodiment, said host cell is a mammalian cell and in another preferred embodiment, said phosphatase is a human phosphatase. In yet another preferred embodiment, said phosphatase is an alkaline phosphatase. The method of the invention can be used to produce wild type (or natural or non-genetically modified) phosphatase and can equally well be used to produce a genetically modified phosphatase, for example any of the herein described phosphatases.

In a further preferred embodiment, the invention provides a method for producing a phosphatase comprising culturing a host cell capable of expressing said phosphatase in a medium comprising $Zn^{2+}$ and allowing the cell to produce said phosphatase, said method further comprising isolating said phosphatase. The invention further provides a phosphatase obtainable by a method for producing a phosphatase comprising culturing a host cell capable of expressing said phosphatase in a medium comprising $Zn^{2+}$ and allowing the cell to produce said phosphatase.

Whether or not the herein described (genetically) modified phosphatases have a certain specific activity, a certain substrate specificity or a certain stability (e.g. pH, temperature, in vivo half-life time) can easily be tested by the skilled person by using commercially available substrates and measuring with commercially available kits inorganic phosphate release upon incubation with alkaline phosphatase. Moreover, it is also possible to use the tests described herein in the experimental part to determine whether the modified phosphatases have any biological relevant activity.

As already mentioned the herein described (genetically) modified phosphatases are useful in diagnostics and in therapy. In one of the embodiments the invention provides a pharmaceutical composition comprising a modified phosphatase, for example:
- an isolated or recombinant alkaline phosphatase comprising a crown domain and a catalytic domain and wherein said crown domain and said catalytic domain are obtained from different alkaline phosphatases or
- an isolated or recombinant phosphatase comprising a modification in the glycosylphosphatidylinositol (GPI) signal sequence and wherein said modification results in a secreted phosphatase or
- an isolated or recombinant phosphatase comprising a mutation in the vicinity of a catalytic residue;
- Or any combination thereof.

Said pharmaceutical composition optionally comprises a pharmaceutical acceptable carrier, diluent or excipient.

The pharmaceutical composition may be presented in any form, for example as a tablet, as an injectable fluid or as an infusion fluid etc. Moreover, the (genetically) modified phosphatase can be administered via different routes, for example intravenously, rectally, bronchially, or orally. Yet another suitable route of administration is the use of a duodenal drip.

In a preferred embodiment, the used route of administration is intravenously. It is clear for the skilled person, that preferably an effective amount of a (genetically) modified phosphatase is delivered. As a start point 1-5000 U/kg/day can be used. If the intravenous route of administration is used, a (genetically) modified phosphatase (at least for a certain amount of time) is preferably applied via continuous infusion.

The compositions may optionally comprise pharmaceutically acceptable excipients, stabilizers, activators, carriers, permeators, propellants, desinfectants, diluents and preservatives. Suitable excipients are commonly known in the art of pharmaceutical formulation and may be readily found and applied by the skilled artisan, references for instance Remmington's Pharmaceutical Sciences, Mace Publishing Company, Philadelphia Pa., 17th ed. 1985.

For oral administration, the secretable AP can, for example, be administered in solid dosage forms, such as capsules, tablets (preferably with an enteric coating), and powders, or in liquid dosage forms, such as elixirs, syrups, and suspensions. AP can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable colour, taste, stability, buffering capacity, dispersion or other known desirable features are red iron oxide, silica gel, sodium lauryl sulphate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain colouring and flavouring to increase patient acceptance.

In a preferred embodiment the compositions comprising a source of a (genetically) modified phosphatase are suitable for oral administration and comprise an enteric coating to protect the AP from the adverse effects of gastric juices and low pH. Enteric coating and controlled release formulations are well known in the art. Enteric coating compositions in the art may comprise of a solution of a water-soluble enteric coating polymer mixed with the active ingredient(s) such as a (genetically) modified phosphatase and other excipients, which are dispersed in an aqueous solution and which may subsequently be dried and/or pelleted. The enteric coating formed offers resistance to attack of a (genetically) modified phosphatase by atmospheric moisture and oxygen during storage and by gastric fluids and low pH after ingestion, while being readily broken down under the alkaline conditions which exist in the lower intestinal tract.

The above described pharmaceutical compositions are very useful in the treatment of for example sepsis, inflammatory bowel disease or other inflammatory disease, and/or renal failure.

In another embodiment therefore, the invention provides a (genetically) modified phosphatase as described herein for use as a medicament, preferably for treating sepsis, inflammatory bowel disease, renal failure, and inflammations preferably selected from the group consisting of rheumatoid arthritis, asthma, chronic obstructive pulmonary disease, atherosclerosis, inflammatory bowel disease, sepsis, neurodermitis and diseases depicted in Table 10.

In yet another embodiment, the invention provides the use of a (genetically) modified phosphatase as described herein in the preparation of a medicament for the treatment of sepsis, inflammatory bowel disease or other inflammatory disease, and/or renal failure.

Sepsis is considered present if infection is highly suspected or proven and two or more of the following systemic inflammatory response syndrome (SIRS) criteria are met:
 Heart rate >90 beats per minute
 Body temperature <36 (96.8° F.) or >38° C. (100.4° F.)
 Hyperventilation (high respiratory rate)>20 breaths per minute or, on blood gas, a $P_aCO_2$ less than 32 mm Hg
 White blood cell count <4000 cells/mm$^3$ or >12000 cells/mm$^3$ (<4×10$^9$ or >12×10$^9$ cells/L), or greater than 10% band forms (immature white blood cells).

Consensus definitions however continue to evolve with the latest expanding the list of signs and symptoms of sepsis to reflect clinical bedside experience. The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS." Patients are defined as having "severe sepsis" if they have sepsis plus signs of systemic hypoperfusion; either end organ dysfunction or a serum lactate greater then 4 mmol/dL. Patients are defined as having septic shock if they have sepsis plus hypotension after an appropriate fluid bolus (typically 20 ml/kg of crystaloid). The invention provides the insight that a (genetically) modified phosphatase according to the invention is especially suitable for the treatment of sepsis. In case of sepsis a (genetically) modified phosphatase as described herein is preferably administrated intravenously.

Inflammatory bowel disease (IBD) is a group of inflammatory conditions of the large intestine and, in some cases, the small intestine. The main forms of IBD are Crohn's disease and ulcerative colitis (UC). Accounting for far fewer cases are other forms of IBD: Collagenous colitis, Lymphocytic colitis, Ischaemic colitis, Diversion colitis, Behçet's syndrome, Infective colitis, Indeterminate colitis. The main difference between Crohn's disease and UC is the location and nature of the inflammatory changes in the gut. Crohn's can affect any part of the gastrointestinal tract, from mouth to anus although a majority of the cases start in the terminal ileum. Ulcerative colitis, in contrast, is restricted to the colon and the anus. Microscopically, ulcerative colitis is restricted to the mucosa (epithelial lining of the gut), while Crohn's disease affects the whole bowel wall. Finally, Crohn's disease and ulcerative colitis present with extra-intestinal manifestations (such as liver problems, arthritis, skin manifestations and eye problems) in different proportions. In rare cases, patients have been diagnosed with both Crohn's disease and ulcerative colitis, though whether it is a combination or simply unidentifiable as one or another is uncertain. Although very different diseases, both may present with any of the following symptoms: abdominal pain, vomiting, diarrhea, hematochezia, weight loss and various associated complaints or diseases (arthritis, pyoderma gangrenosum, primary sclerosing cholangitis). Diagnosis is generally by colonoscopy with biopsy of pathological lesions. In case of IBD a (genetically) modified phosphatase as described herein is preferably administrated via an enteric coated tablet or via duodenal drip.

Next to the group of inflammatory bowel disease, the invention provides the insight that a phosphatase according to the invention is suitable for treating other inflammatory diseases. Inflammatory diseases can affect diverse organs, such as lungs, joints, liver, pancreas, skin, or even nervous tissue. Table 10 gives an unlimiting list of organs which may be inflammatory affected. A wide variety of etiologic agents have been shown to cause or sustain such inflammatory diseases. Non-limiting examples of said etiologic agents are microbes (bacteria, fungi, virii), allergens, autoimmune, trauma, and ischemia/reperfusion. Although the causative agent and etiology may be very diverse, (sub)chronic inflammation results from a deranged immune reaction. It is commonly thought that such derailed immune reaction is sustained through a vicious spiral that includes inflammation-induced tissue damage that in turn activates the immune system. Amongst others, ATP has been shown to play a role in the above mentioned vicious spiral. The invention provides the insight that a (genetically) modified phosphatase as described herein, is able to dephosphorylate ATP and thus break said vicious spiral, which is beneficial to the individual suffering from said inflammatory disease. When treating such an inflammatory disease, a (genetically) modified phosphatase according to the invention is preferably administrated intravenously or, if feasible locally, for instance. intra-articular in the case of rheumatoid arthritis, intrathecal in the case of inflammation of the (cenral) nervous system, intrabronchial in the case of (allergic) asthma, or topical in the case of e.g. neurodermitis. Furthermore, (sub)chronic inflammatory reactions, such as sepsis, Crohn's disease, rheumatoid arthritis and the like, have been described to be accompanied with (serum) zinc deficiencies. A phosphatase according to the invention, wherein said phosphatase does not lose its enzymatic activity when provided in a zinc deficient environment, is especially suitable for treating said inflammatory diseases.

The invention provides the insight that a phosphatase according to the invention, wherein said phosphatase comprises a catalytic domain of ALPI and a crown domain of ALPP retains its activity at sub-physiological $Zn^{2+}$ concentrations as low as 0.01 µM.

In one embodiment therefore, the invention provides for the use of a phosphatase comprising a catalytic domain of ALPI and a crown domain of ALPP for the dephosphorylation of a substrate, preferably an adenosine phosphate, in an environment comprising a $Zn^{2+}$ concentration lower than 10 µM, preferably a $Zn^{2+}$ concentration lower than 1 µM, more preferably a $Zn^{2+}$ concentration lower than 0.1 µM.

Acute renal failure (ARF) is defined as an acute loss of kidney function that results in an increase of the serum creatinine level. In acute renal failure, the glomerular filtration rate decreases over days to weeks. As a result, excretion of nitrogenous waste is reduced, and fluid and electrolyte balances cannot be maintained. Patients with acute renal failure are often asymptomatic, and the condition is diagnosed by observed elevations of blood urea nitrogen (BUN) and serum creatinine levels. Complete renal shutdown is present when the serum creatinine level rises by at least 0.5 mg per dL per day and the urine output is less than 400 mL per day (oliguria). The herein described (genetically) modified phosphatases can not only be used in the treatment of renal failure but also to improve renal function, especially in cases where the renal function is at least partly impaired/reduced. In a preferred embodiment, the used route of administration is intravenously. It is clear for the skilled person, that preferably an effective amount of a (genetically) modified phosphatase is delivered. As a start point 1-5000 U/kg/day can be used. If the intravenous route of administration is used, a (genetically) modified phosphatase (at least for a certain amount of time) is preferably applied via continuous infusion.

In yet another embodiment, the invention provides a method for treating a subject suffering from sepsis, inflammatory bowel disease or other inflammatory disease, and/or renal failure comprising administering to said subject an effective amount of any of the herein described modified phosphatases.

Besides the fact that a (genetically) modified phosphatase as described herein can be incorporated in a pharmaceutical composition such a phosphatase can also be part of a nutritional composition.

In a preferred embodiment of the current invention the source of a (genetically) modified phosphatase is a (genetically) modified phosphatase which is preferably produced or isolated from milk, preferably bovine milk. The milk may be obtained from animals that have been bred or genetically modified to produce elevated levels of a (genetically) modified phosphatase in their milk as compared to wild-type animals. The preparation of a (genetically) modified phosphatase enriched fractions from milk is known in the art. For instance the milkfat globule membrane enriched or derived fraction is the preferred a (genetically) modified phosphatase enriched milk fraction and may be routinely obtained by conventional skimming of raw milk. A (genetically) modified phosphatase isolated from milk may be formulated in pharmaceutical compositions and in food compositions or in nutraceuticals.

In a preferred embodiment a (genetically) modified phosphatase containing composition for oral administration of a (genetically) modified phosphatase to the mucosa of the gastrointestinal tract according to the current invention is a food product or nutraceutical enriched for a (genetically) modified phosphatase. In one embodiment the food product may be a plant, fruit or vegetable, optionally genetically modified to contain an enhanced level of a (genetically) modified phosphatase. In another embodiment a (genetically) modified phosphatase containing food product or nutraceutical is a dairy product. In particular preparations and compositions containing non-pasteurised milk or fractions thereof, preferably bovine milk, contain high levels of a (genetically) modified phosphatase and are particularly suited for oral administration as a source of a (genetically) modified phosphatase according to the current invention.

The current invention also pertains to a method for the preparation of a (genetically) modified phosphatase enriched dairy product, preferably milk, a milk fraction or milk product. The method comprises the fractionation of raw milk, preferably bovine milk, pasteurisation of the fractions not containing or not rich in a (genetically) modified phosphatase and reformulating said fractions with the unpasteurised, a (genetically) modified phosphatase rich fractions, to obtain a less perishable and a (genetically) modified phosphatase enriched dairy product. The non pasteurised a (genetically) modified phosphatase rich fractions may be sterilised by other means, such as, but not limited to, irradiation with UV-, X- or gamma-rays, filtration, pressure, osmotic pressure, chemicals or antibiotics, ensuring that the a (genetically) modified phosphatase enzyme remains substantially active and that the milkfraction becomes substantially sterile. This dairy product may be used in compositions or administered directly to subjects suffering from or at risk of developing sepsis, IBD or renal failure. However, a (genetically) modified phosphatase enriched dairy product may also be offered to healthy subjects as a pharmaceutical or nutraceutical product for the preservation of intestinal structural integrity.

Moreover, a modified phosphatase of the invention can also be added to a nutrient (such as milk) instead of being produced in said nutrient. Moreover, tablets and/or capsules can be prepared which are subsequently added to a nutrient or which can be taken directly by a human being.

The invention will be explained in more detail in the following, non-limiting examples.

Experimental Part

Materials and Methods

Example 1

Dephosphorylation of the Biologically Active Substrate ATP by Different Phosphatases ATPlite™ Kit Obtained from Perkin Elmer Containing the Following Reagents:
Mammalian lysis solution, Substrate buffer solution, Lyophilized substrate solution and Lyophilized ATP standard.
Preparation of Lyophilized ATP Standard:
Reconstitute a vial of lyophilized ATP standard solution with MiliQ so that a 10 mM stock solution is obtained. After addition of MiliQ, allow ATP to dissolve completely by swirling for one minute.
Determination of ATP Dephosphorylating Activity:
Prepare 6 standard curves with a start concentration of 20 µM ATP and make a serial dilution. Final volume should be 100 µl per well
Prepare a phosphatase enzyme activity of 1 U/ml. Prepare 3 standard curves with start concentration 1 U/ml and make a serial dilution. Final volume should be 50 µl.
Prepare a 40 µM ATP solution
Add together 50 µl of the 1 U/ml phosphatase enzyme solution standard curve and 50 µl of the 40 µM ATP solution in a 96-well black Optiplate™ (Perkin Elmer). The final volume in each well will be 100 µl.
Shake plate and incubate 90 min. by 37° C.
Allow the reagents to equilibrate to room temperature
Reconstitute one lyophilized substrate solution vial by adding the proper amount of substrate solution buffer, according to the manufacturer's recommendations. Agitate gently until the solution is homogeneous,
Add 50 µl of the mammalian cell lysis solution and shake the plate for 5 minutes at 700 rpm.
Add 50 µl of the substrate solution to the well and shake the plate for 5 minutes at 700 rpm.
Remove air bubbles by spraying alcohol 70% over plate
Dark adapt the plate for 10 minutes and measure the luminescence on the Viktor3™ Multi Label Reader (Perkin Elmer)

Example 2

Liver-Slice Assay Using Different Isoforms of Alkaline Phosphatase

Rats were sacrificed under $O_2/N_2O$/Forene anaesthesia and livers were taken out and stored in University of Wisconsin organ preservation solution (UW) until slice preparation. Cores (diameter, 5 mm) were made from the pieces of liver tissue and stored in ice-cold UW solution until slicing. The slicing was performed with a Krumdieck slicer. Ice-cold KHB supplemented with glucose to a final concentration of 25 mM was used as slice buffer. Rat liver slices (thickness, 200-250 µm; wet weight, ±3 mg) were prepared with standard settings (cycle speed, 30; interrupted mode). After slicing, the rat liver slices were stored in UW solution until the start of the experiment.

Slices were incubated individually at 37° C. in 12-well plates (Greiner, Alphen a/d Rijn, The Netherlands) in 1.3 ml Williams' medium E supplemented with Glutamax I (Gibco BRL, Paisly), Scotland). 50 mg/ml gentamicin (Gibco BRL) and saturated with 95% $O_2$/5% $CO_2$. Slices were incubated for 24 hr with or without 10 µg/ml LPS and with or without different isoforms of AP in different concentrations. Medium of the slices were stored at −80° C. until $NO_x$ measurement.

NO (the sum of NO, $NO_2$ and $NO_3$) was measured by adding 5 µl of a mixture of 0.275 µl 100 mM NADPH, 2.2 µl 10 U/ml nitrate reductase, and 0.055 µl 10 mM FAD, which was diluted 2-fold in water, to 110 µl of supernatant. After 30 minutes incubation at 37° C., 5 µl of a second mixture; 2.2 µl Na-pyruvate 0.5 M and 0.55 µl of 5 mg/ml LDH, diluted 1:0.82 in water, was added. After 5 minutes incubation at 37° C., 5 µl of 30% $ZnSO_4$ was added and samples were centrifuged at 2000 rpm. 100 µl of the supernatant was then transferred to a new plate and mixed with 100 µl of Griess-reagens containing 0.1% sulphanilamide, 0.01% n-Naphtyl-Ethylene-Diamin and 2.5% phosphoric acid. Finally, absorbance was measured at 550 nm on a microplate reader. The absorbance was related to the absorbance of a standard curve of sodium nitrate.

Example 3

Biological Effect, of Dephosphorylation of Extracellular ATP

The murine macrophage cell line RAW264.7 and the human epithelial cell lines T84 (colorectal carcinoma) were obtained from the American Type Culture Collection (ATCC, Rockville, Md., USA) and were maintained in DMEM/F12

(1:1) and DMEM medium containing 4.5 g/l glucose, respectively. Both media were obtained from Invitrogen Corp. (Breda, The Netherlands), contained Glutamax I and were supplemented with 10% heat-inactivated FBS (Wisent Inc. (Quebec, Canada), 100 U/ml penicillin and 100 µg/ml streptomycin (both from Intvitrogen Corp.). T84 cell line was subcultured at confluence by employing trypsin-EDTA, RAW264.7 cells were scraped using a rubber policeman.

$4 \times 10^5$ T84 cells were plated into 12 well plates (Nunc, Roskilde, Denmark) with 2 ml of medium. On reaching confluency, medium was refreshed and cells were incubated with (FIG. 3) or without (FIG. 2) 1 µg/ml LPS for 2 hours in the presence or absence of different concentrations of ATP and/or AP as depicted in Figures (checkerboard). After 2 hours, the supernatant was collected and transferred into 24 well plates containing RAW264.7 cells. These RAW264.7 cells were plated the day before into 24 well plates (Nunc, Roskilde, Denmark) at a density of $2 \times 10^5$ in one ml of medium. Prior to transfer of 1 ml of the supernatants of the T84 cells, the supernatant of the RAW was aspirated and discarded.

The RAW cells were incubated with the T84 supernatants for 24 hours at 37° C. at 5% $CO_2$, before the supernatants were collected and checked for cytokine (IL-6, TNFα) content using a commercial available ELISA (Biosource Europe SE, Nivelles, Belgium).

Example 4

Preparation of Mutants

The mutants as herein in described and more specific the mutants as described in Tables 4, 5 and 6 are/were prepared by using standard molecular biology techniques.

The amino acid positions as mentioned in Tables 4 to 6 correspond to the sequences as depicted in FIG. 1. Only the mutated positions are indicated, i.e. only the deviations from the wild type sequences are given. For example mutant 1 of Table 4 is, if compared to the given wild type sequence, unchanged at positions 87, 93 and 429, i.e. position 87 is a K, position 93 is a G and position 429 is an E.

The mutants will be prepared and checked by standard molecular biology techniques, such as PCR site-directed mutagenesis, restriction enzyme analysis, and sequence analysis.

Example 5

At t=0 different recombinant alkaline phosphatases containing 450±50 Units were diluted 4000× in diluent buffer (0.025M glycine/NaOH pH 9.6/1 mM MgCl2/1% mannitol/ 0.05% BSA) with different concentrations of $Zn^{2+}$. In a second example, BSA as a possible $Zn^{2+}$ source was omitted from the buffer. Within 1 minute after dilution (T=0), a sample was taken and measured for alkaline phosphatase activity using the pNPP assay described below. 90 min (T=1½ h), 180 min (T=3 h) and 22 hour (T=22 h) later, each time a sample was taken and directly measured for alkaline phosphatase activity using the pNPP assay as described below. Activity in U/ml was backcalculated by the specific activity (U/mg) by dividing the obtained result in U/ml through the protein content previously obtained using a commercially available BCA kit (Pierce).

pNPP Phosphatase Activity Measurement:
Working Substrate:
Temperature of reagents, substrates, samples and incubation chamber were set to 25° C. The spectrophotometer was set to a wavelength of 405 nm and the light path was 1 cm.

In a disposable cuvette 50 µl of the test substance and 1450 µl of the working substrate were pipetted, mixed and immediately the cuvette was placed in the spectrophotometer and the increase in absorbance at 405 nm was recorded for 3 minutes. The activity per volume was calculated using the following equation:

$$\text{activity(U/ml)} = \Delta E405/\min \times 1.6 \times \text{dilution factor}$$

Note: measurement range should be between 0.04 and 0.4 U/ml

Example 6

Effect of pH on Stability of Different Phosphatases

The pH stability of transiently expressed alkaline phosphatases in HEK293 cells was investigated. A pH range of 4.0-9.0 was tested using 5 different 0.1M (sodium acetate, MES (2-(N-morpholino)ethanesulfonic acid), MOPS (3-N-morpholino)propanesulfonic acid), Tris (2-amino-2-hydroxymethyl-propane-1,3-diol) and glycine) buffers adjusted for their specific pH at 25° C. BiAP stabilized with 1% mannitol was used as reference. The alkaline phosphatase solutions were diluted in the respective buffers to approximately 100 U/ml, stored for 24 h at room temperature and determined for enzymatic activity using the pNPP phosphatase activity assay as described above.

Example 7

Effect of Zinc on the Expression of the Different Phosphatases

The influence of different zinc salts on the activity of transiently expressed alkaline phosphatases in HEK293 cells was investigated using small scale transfections in culture medium supplemented with 1 mM MgCl2+0.1 mM Zinc salt (ZnCl2, or ZnSO4 or ZnAc2). HEK293 cells were transfected with shIAP, shPLAP, Xinplap (catALPI/crownALPP) and sALPP-ALPI-CD (catALPP/crownALPI) and at t=144 h samples were taken and analysed for enzymatic activity using the pNPP phosphatase activity assay as described above.

Example 8

Effect of Zinc on the Stability of the Different Phosphatases

Solutions containing approximately 20 U/ml of different (recombinant) isoforms of alkaline phosphatase in the presence or absence of 100 µM of $ZnCl_2$ were prepared for temperature stability testing. The samples were stored at RT, 37° C. and 56° C. and enzyme activity (pNPP) was determined at t=0, 2 h and 24 h using the pNPP phosphatase activity assay as described above.

Example 9

Generation of Fusion Proteins and Mutants of Alkaline Phosphatase

To select a suitable expression system, the human intestinal (hIAP) and human placental (hPLAP) cDNA, coding for the mature proteins, either with or without the GPI anchor sequence, were cloned into several vectors. After small scale infections, the expression vector used was CMV driven, contained the cystatin signal sequence and harbored the N-terminal HIS tag to facilitate purification. After successfully expressing both secretable hIAP and hPLAP, two fusion human secretable alkaline phosphatases were constructed in silico, one based on the backbone of intestinal AP containing the placental crown domain (aa 360-430 of the mature sequence) and the second based on the backbone of placental AP with the crown domain of intestinal AP (the first referred to as RecAP or catALPI/crownALPP and second referred to as shPLAP-shIAP-CD or catALPP/crownALPI). The two genes were synthesized containing the human cystatin signal sequence and cloned in the CMV promotor containing expression vector.

Example 10

Effect of GPI Anchor on Phosphatase Specific Activity

Several recombinant forms of AP were produced, purified and evaluated for enzymatic activity using the pNPP phosphatase activity assay as described above. Furthermore, protein amount in the samples was measured using SDS-PAGE and GelEval software. Specific activity was calculated by dividing activity (U/ml) by protein concentration (mg/ml) and expressed as U/mg.

Experimental Part

Results

Example 1

Dephosphorylation of the Biologically Active Substrate ATP by Different Phosphatases ATP at a final concentration of 20 µM was incubated with different concentrations of BIAP, sALPP, sALPI or the chimera catALPI/crownALPP. From Table 9 it is obvious that pNPP chemical activity is not 1:1 related to the activity towards a biological substrate, e.g. ATP. Whereas BIAP and sALPI show more than 50% dephosphorylation of ATP after 90 minutes at 37° C. at concentrations of 0.031 and 0.004 pNPP units, respectively, ALPP and catALPP/crownALPP can only dephosphorylate this amount at concentrations of 0.125 and 0.0625 pNPP units, respectively.

Example 2

Liver-Slice Assay Using Different Isoforms of Alkaline Phosophatase

Figure 6:
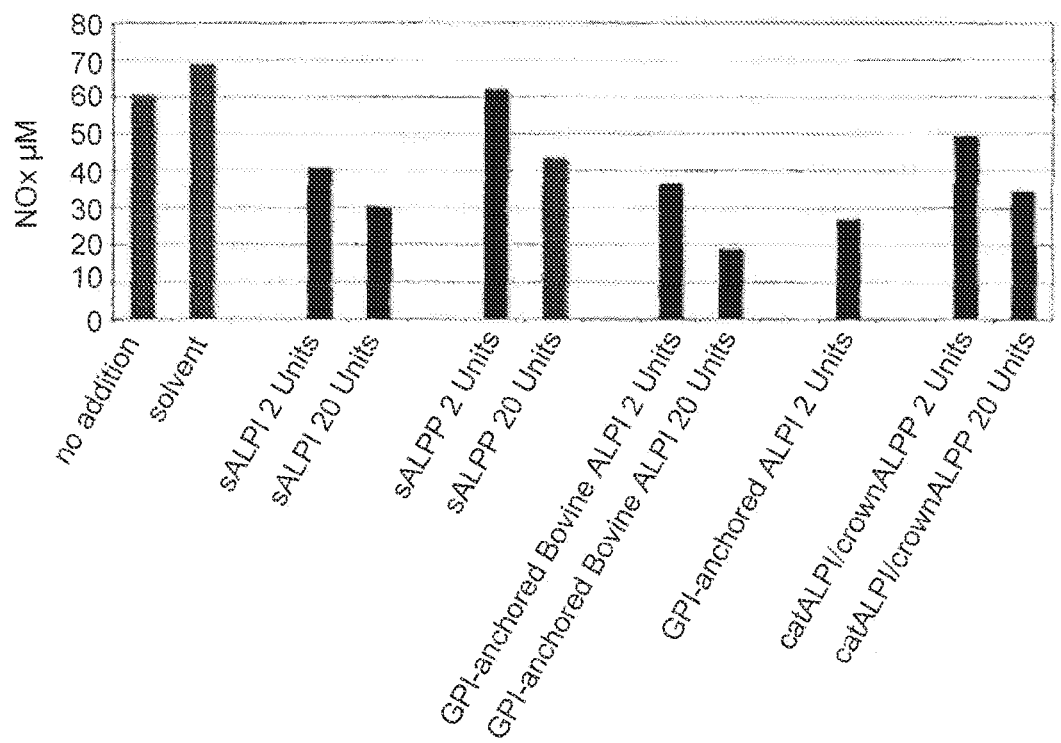

Upon stimulation with LPS (10 µg/ml), liver slices produce NOx. FIG. 6 shows that in the presence of different recombinant human alkaline phosphatases (sALPI, sALPP, GPI-anchored ALPI, catALPI/crownALPP) at different concentrations, the NOx production was significantly inhibited. In this experiment, bovine derived ALPI was used as a positive control and solvent as a negative control.

Without the addition of LPS, NOx production by the liver slices was less then 10 µM and was not significantly altered by the presence of the different phosphatases during incubation (data not shown). From this it is concluded that all tested recombinant isoforms of human alkaline phosphatases, regardless of the presence of a GPI anchor have activity towards a biological substrate that is involved in the LPS-induced NOx production.

Example 3

Biological Effect of Dephosphorylation of Extracellular ATP

Figure 3:
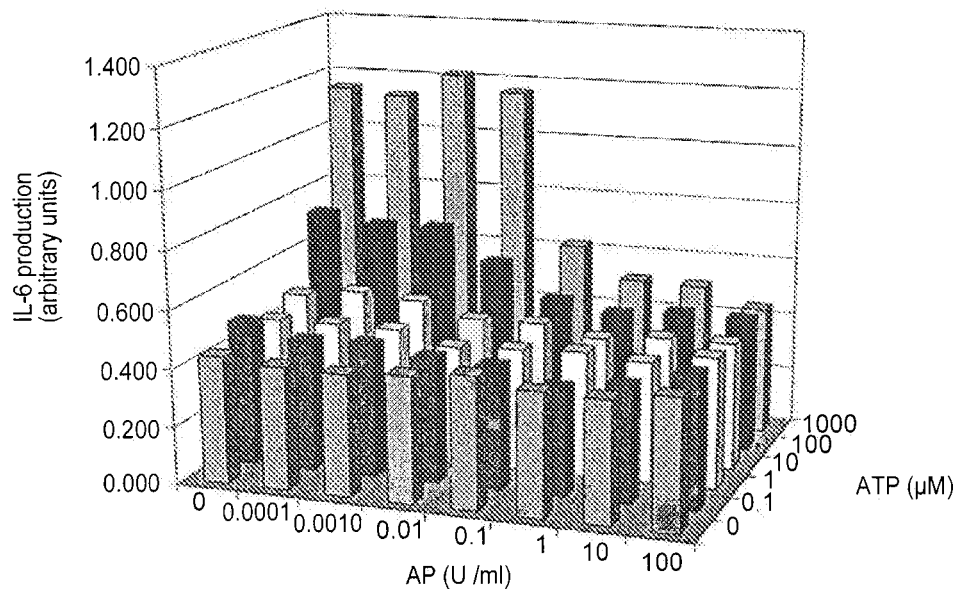

The production of IL-6 by RAW264.7 cells upon incubation with T84 supernatant was dependent on LPS. Without LPS (FIG. 2), low levels of IL-6 were produced. ATP as well as AP could not alter the levels of IL-6 produced by RAW264.7 cells. In contrast, when LPS was present, the production of IL-6 by RAW264.7 incubated with T84 supernatant increased with increasing concentrations of ATP. This increase in cytokine production by ATP could be completely diminished by AP concentrations of 0.1 U/ml and higher (FIG. 3).

Similar results (not shown) were obtained for TNF using the same protocol and for TNFα and IL-6 using HT29 instead of T84 as a source of epithelial cells.

It is concluded that AP dephosphorylates ATP and thereby decreases its LPS-potentiating effect. It is unlikely that AP dephosphorylates LPS as no effect of AP on LPS was seen. The combination of ATP and LPS could only be diminished by AP to levels equal to LPS alone.

Example 5

Determination of $Zn^{2+}$ Dependency of Different Phosphatases

Figure 4:
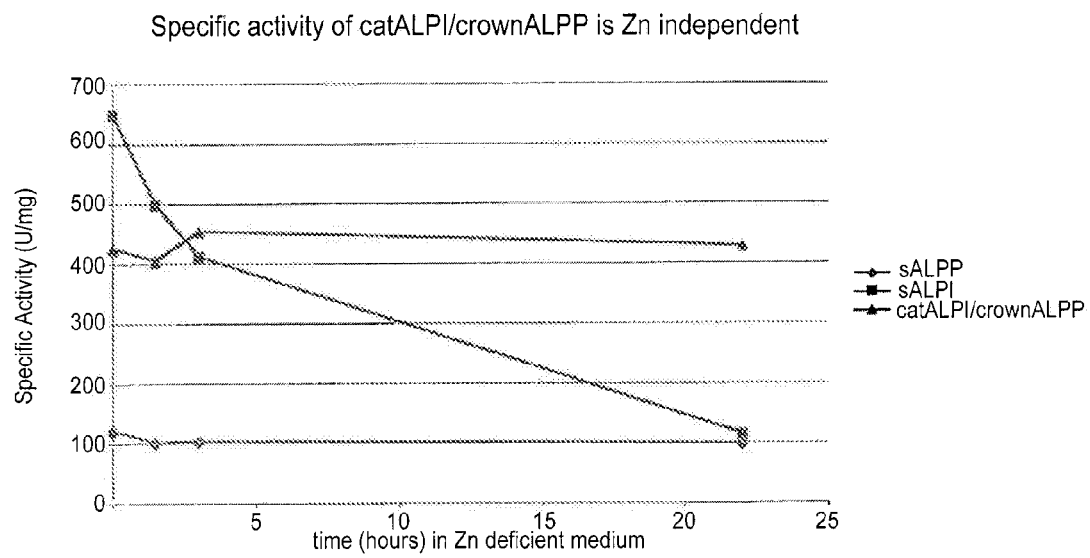
Figure 5:
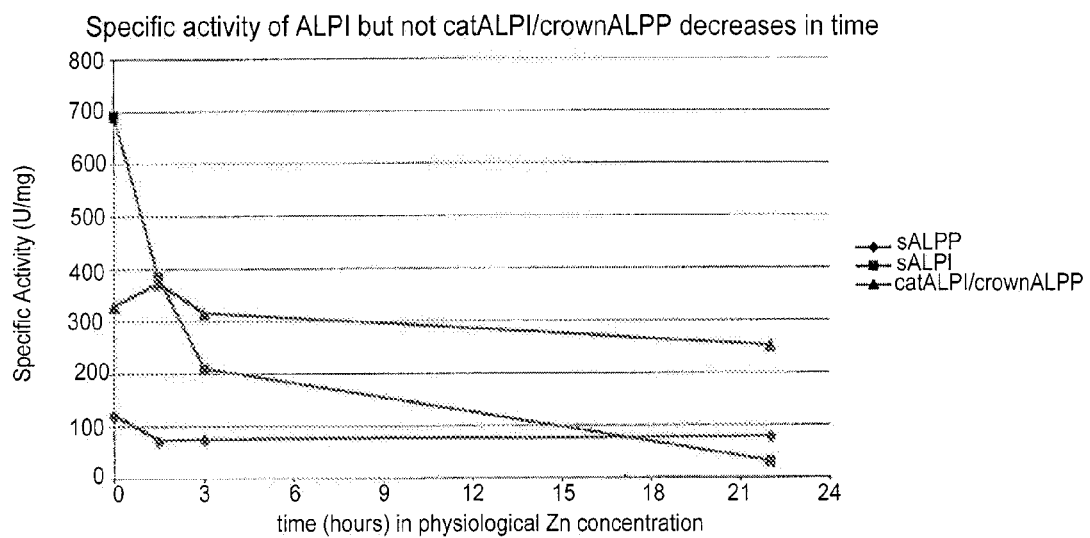

As depicted in FIG. 4 and Table 7, $Zn^{2+}$ significantly stabilized the specific activity of sALPI, whereas sALPP and the chimer catALPI/crownALPP retained their initial specific activity independent of the presence of $Zn^{2+}$ in the medium. In this experiment, BSA, routinely used in the pNPP phosphatase activity assay, may be a source of trace amounts of $Zn^{2+}$. Therefore a second experiment was performed. Table 8 and FIG. 5 show that in the absence of BSA and in the presence of $Zn^{2+}$ depleting chelator EDTA, all isoforms lose their specific activity after 22 h. However addition of physiological (0.5-10 nM) concentrations of $Zn^{2+}$ during storage and during the reaction preserved more than 60, respectively 75% of the initial specific activity of sALPP and catALPI/crownALPP, whereas more than 95% of the initial specific activity of sALPI was lost. Unphysiologically high concentrations of $Zn^{2+}$ were necessary to preserve sALPI's specific activity.

It is therefore concluded that the chimer catALPI/crownALPP shows high specific activity, comparable with that of sALPI, combined with $Zn^{2+}$ independent specific activity, comparable with that of sALPP. It is concluded that the $Zn^{2+}$ dependency is located in the sALPI crown domain, whereas the high specific activity is located in the sALPI catalytic domain.

Example 6

Effect of pH on Stability of Different Phosphatases

Figure 7:
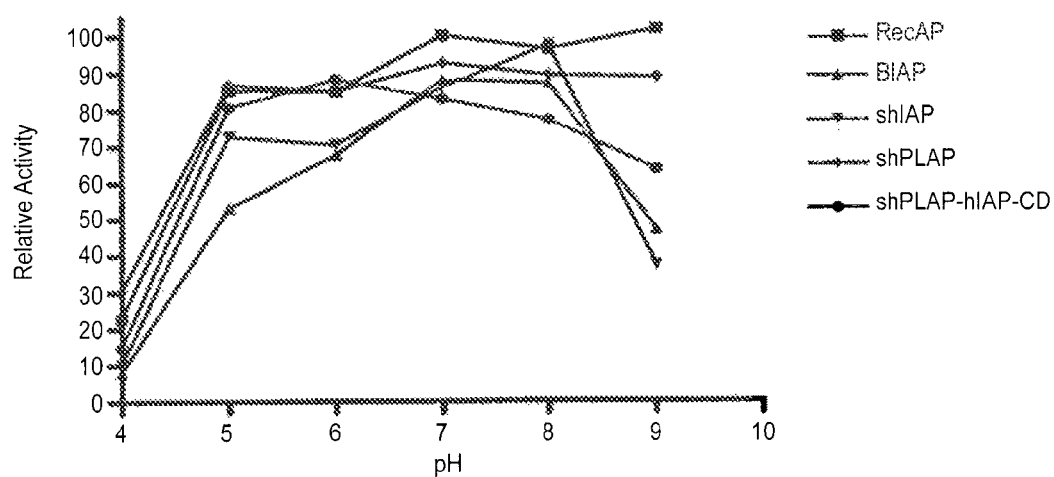
FIG. 7 shows the placental type is more stable than the intestinal isoforms.

BiAP, shIAP, shPLAP, RecAP were diluted and stored in 0.1M (sodium acetate, MES (2-(N-morpholino)ethane-sulfonic acid), MOPS (3-N-morpholino)propanesulfonic acid), Tris (2-amino-2-hydroxymethyl-propane-1,3-diol) and glycine) buffers with pH values of 4.0, 5.0, 6.0, 7.0, 8.0 and 9.0 at RT for 24 h. For each pH value the initial enzyme activity and the enzyme activity after storage was determined according to the standard pNPP assay. As expected and indicated by its name, alkaline phosphatase activity is optimal in the high pH range (alkaline environment). However, as FIG. 7 shows, the placental type is more stable than the intestinal isoforms. Furthermore, the results demonstrate that this stability, especially in the high pH range, is determined by the crown domain and not by the catalytic domain, as catALPI/crownALPP (recAP) follows the stability profile of the shPLAP and is stable between pH 5-9, whereas the stability of the BIAP and shIAP is restricted to pH 7-8. In contrast, catALPP/crownALPI (shPLAP-hIAP-CD) is less stable than the placental type AP and catALPI/crownALPP at pH 9. This demonstrates that catALPI/crownALPP retains its activity in a much broader range of pH values than the native APs or the reverse chimer (catALPP/crownALPI) tested.

Example 7

Effect of Zinc on the Expression of Different Phosphatases

Using small scale transfections in HEK293 cells, the influence of different zinc salts on the activity of transiently expressed alkaline phosphatases was investigated. In order to do so, shIAP, shPLAP, Xinplap (catALPI/crownALPP) and sALPP-ALPI-CD (catALPP/crownALPI) were transfected and at t=144 h samples were taken and analysed for enzymatic activity. The obtained results revealed that there was a concentration dependency for Zn2+ ions regarding the enzymatic activity, but that the increase of activity observed was independent for the type of zinc salt used.

Figure 8:
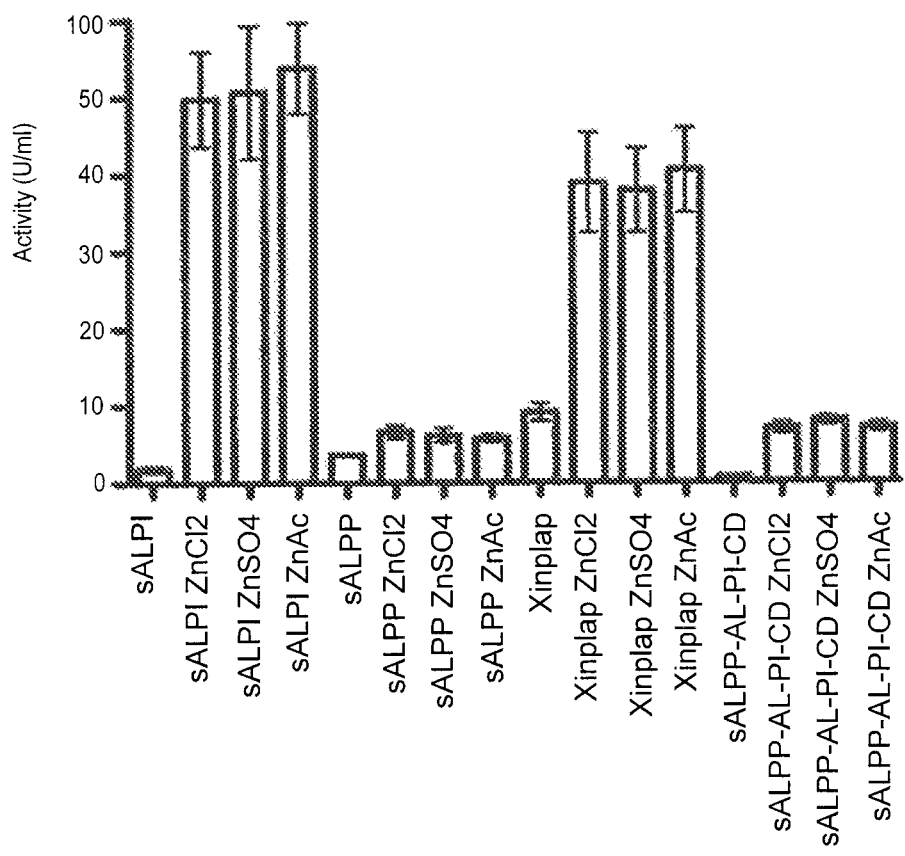
FIG. 8 Influence of different zinc salts added to the culture medium during production of different recombinant alkaline phosphatases on the enzymatic activity. The obtained enzyme activity is dependent on zinc, but that it is independent of which kind of zinc salt is used.

From the results presented in FIG. 8 it is concluded that the obtained enzyme activity is dependent on zinc, but that it is independent of which kind of zinc salt is used. Furthermore, it was shown that addition of zinc is most favorable for the production of shIAP with an induction factor for enzyme activity of >30. For sALPP and Xinplap the activity enhancement was <2 and >4, respectively. The reverse chimer (sALPP-ALPI-CD, also called catALPP/crownALPI) showed negligible activity if produced in the absence of zinc, whereas it obtained activity comparable with sALPP in the presence of zinc.

Furthermore, Xinplap showed a much higher enzymatic activity without the addition of Zn/Mg ions than any of the other tested APs (factor 5) and is less dependent on Zn/Mg as compared to shIAP or the reverse chimer, catALPP/crownALPI.

Example 8

Effect of Zinc on the Stability of the Different Phosphatases

Figure 9:
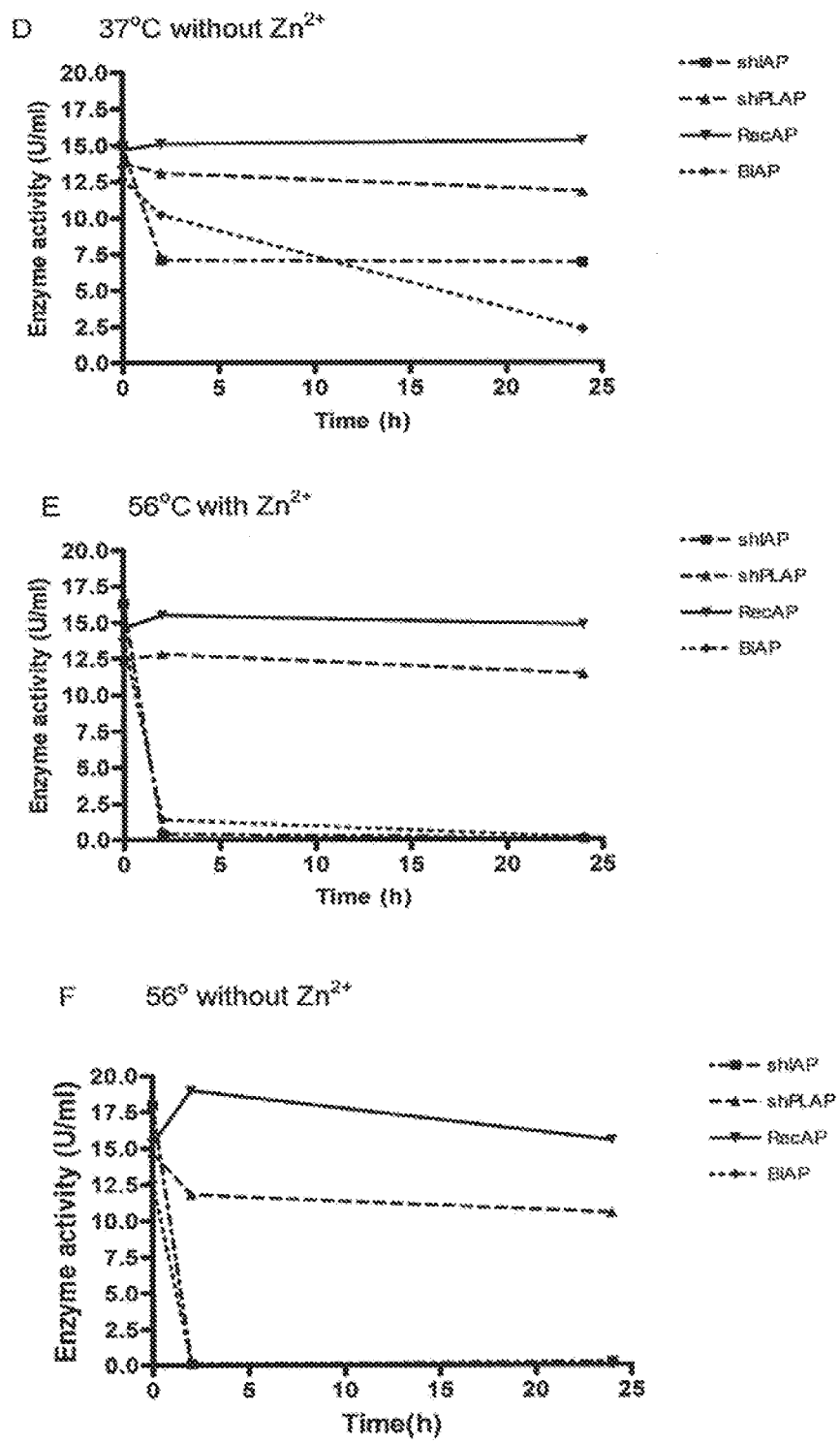
FIG. 9 Stability of the enzymatic activity of different alkaline phosphatases determined after storage in the presence of zinc at: A room temperature, C 37° C. and E 56° C. or in the absence of zinc at B room temperature, D 37° C. and F 56° C.

FIG. 9 shows the stability profile of different APs in time at different temperatures and in the presence or absence of 100 µM ZnCl$_2$. It is concluded from the results that, in the absence of zinc, the intestinal isoforms (sALPI and BIAP) of alkaline phosphatase are highly temperature sensitive with respect to the enzyme activity. At 37° C. BIAP lost 20% of its activity within 2 hours and after 24 h only 20% enzymatic activity remains. shIAP shows a decline in activity of 30% after 24 h storage at 37° C. FIG. 9C shows that the presence of zinc during stability testing at 37° C. protects the enzyme from degradation. However, at 56° C., zinc no longer protects the intestinal isoforms and both lose their enzymatic activity almost completely in the first 2 hours. In contrast, RecAP (catALPI/crownALPP) and shPLAP (sALPP) show excellent stability in the presence or absence of 100 µM up to 22 hours even at 56° C.

Example 9

Generation of Fusion Proteins and Mutants of Alkaline Phosphatase

Figure 10:
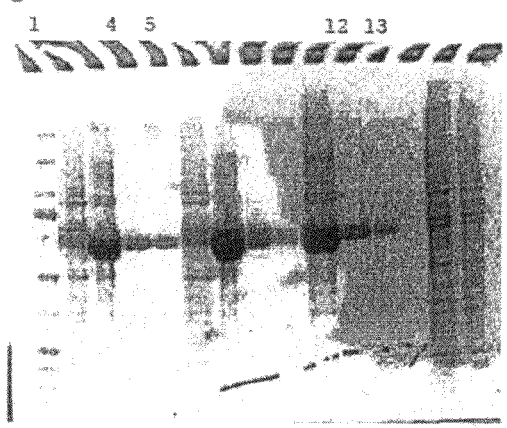
FIG. 10 SDS-PAGE: protein profile of purified secretable hIAP and secretable hPLAP. Lane 1) MW Marker, 4+5) secretable hIAP 10 and 25 times diluted, 12+13) secretable hPLAP 10 and 25 times diluted.

Secretable hIAP and secretable hPLAP were expressed in HEK293 using a CMV promotor driven, cystatin signal sequence containing vector and contained a HIS tag on the N-terminal part of the protein. The expressed proteins were purified through the HIS tag and analyzed by SDS PAGE (see FIG. 10). The protein yield of 1 Liter of suspension culture for secretable hIAP and hPLAP was 38 and 16 mg, respectively and showed >95% purity. The specific activity of hIAP and hPLAP was 21 and 100 U/mg, respectively.

Based upon these two secretable recombinant phosphatases, two domain-swap variants were designed in silico, and expressed in HEK293 cells. A remarkable result was obtained for RecAP, which consists of an intestinal alkaline phosphatase backbone with the crown domain of placental alkaline phosphatase. RecAP showed a five times higher enzymatic activity as compared with secretable hIAP (14 U/ml vs 2.7 U/ml) under conventional culture conditions. However, the addition of zinc salt up to 100 µM during cell culture and phosphatase expression has only minor influence on the enzymatic activity of RecAP (18.8 U/ml vs 14.0 U.ml without addition zinc), whereas it significantly improves activity of secretable hIAP (37.9 U/ml vs 2.7 U.ml without addition of zinc). The domain-swap variant based on the backbone of placental AP with the crown domain of intestinal AP (catALPP/crownALPI) on the other hand, shows zinc dependency comparable with the intestinal form and maximum activity comparable with secretable PLAP. The observed increase in activity of shIAP and catALPP/crownALPI could not be achieved if zinc was added to the enzyme after expression and purification. It is therefore concluded that the addition of 100 µM zinc during expression of alkaline phosphatases, preferably those comprising a crown domain of the intestinal form, results in a higher yield of alkaline phosphatase activity.

Example 10

Effect of GPI Anchor on Phosphatase Specific Activity

Figure 11:
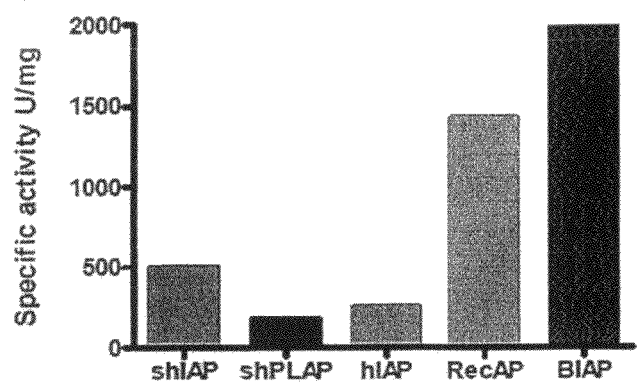
FIG. 11 Specific enzymatic activities of 4 human and a bovine AP against para-nitrophenylphosphate (pNPP), the standard chemical substrate for AP activity determination.

Several recombinant forms of AP were produced and evaluated for enzymatic activity. The results presented in FIG. 11 demonstrate that bovine intestinal alkaline phosphatase (BIAP) and recAP (catALPI/crownALPP) display similar specific activity that is superior to that of secretable hIAP, secretable hPLAP and the GPI-anchored hIAP. The purity of the enzyme is important for the specific enzyme activity. It should therefore be noted that the four human enzymes were purified in a laboratory setting, whereas BIAP is obtained as an ultrapure GMP batch. It should further be noticed that the secretable hIAP has a specific activity that is approximately 2 fold higher than that of GPI-anchored hIAP. Without being limited to theory, the higher specific activity can either be structural related or purity related, as secretable AP is more easily purified than GPI-anchored (membrane bound) AP.

Tables

TABLE 1

HEK293 expression levels (U/ml) of alkaline phosphatases after t = 144 h and the effect on the activity after overnight incubation with 0.1 mM $ZnCl_2$

| Construct | Units/ml | Units/ml after o/n with 0.1 mM $ZnCl_2$ |
|---|---|---|
| sALPP N-his tag | 3.34 | 3.55 |
| sALPP C-his tag | 3.75 | 3.97 |
| sALPI N-his tag | 1.55 | 1.92 |
| sALPI C-his tag | 7.52 | 8.07 |
| Native sALPI | 2.84 | 4.94 |

TABLE 2

HEK 293 expression levels (U/ml) of alkaline phosphatases after t = 144 h and the effect on the activity of different $ZnCl_2$ and/or $MgCl_2$ concentrations in culture medium

| Construct | Enzyme activity in Units/ml | | | | | |
|---|---|---|---|---|---|---|
| | No addition | 0.05 mM $Zn^{2+}$ | 0.1 mM $Zn^{2+}$ | 1 mM $Mg^{2+}$ | 5 mM $Mg^{2+}$ | 0.1 mM $Zn^{2+}$/ 1 mM $Mg^{2+}$ |
| sALPI | 2.2 | 55.8 | 56.6 | 6.4 | 5.9 | 61.3 |
| sALPP | 6.8 | 8.7 | 8.9 | 6.1 | 5.4 | 7.7 |

TABLE 3

HEK 293 expression levels (U/ml) of chimeric alkaline phosphatases after t = 96 h and the effect on the activity of $ZnCl_2$ in culture medium

| Construct | Enzyme activity in Units/ml | |
|---|---|---|
| | No addtion | 0.1 mM $Zn^{2+}$/ 1 mM $Mg^{2+}$ |
| catALPI/crownALPP | 3.72 | 2.43 |

TABLE 4

Mutation-sites in ALPP with proposed amino acid changes

| | Position in mature ALPP | | | | |
|---|---|---|---|---|---|
| Name | 44 | 87 | 93 | 429 | Alternative name |
| wt | M | K | G | E | — |
| mut 1 | L | | | | M44L |
| mut 2 | | R | | | K87R |
| mut 3 | | | A | | G93A |
| mut 4 | | | | S | E429S |
| mut 5 | L | R | | | M44L, K87R |
| mut 6 | L | | A | | M44L, G93A |
| mut 7 | L | | | S | M44L, E429S |
| mut 8 | | R | A | | K87R, G93A |
| mut 9 | | R | | S | K87R, E429S |
| mut 10 | | | A | S | G93A, E429S |
| mut 11 | L | R | A | | M44L, K87R, G93A |
| mut 12 | L | R | | S | M44L, K87R, E429S |
| mut 13 | L | | A | S | M44L, G93A, E429S |
| mut 14 | | R | A | S | K87R, G93A, E429S |
| mut 15 | L | R | A | S | M44L, K87R, G93A, E429S |

TABLE 5

Mutation sites in ALPI with proposed amino acid changes

| | Position in mature ALPI | | | | |
|---|---|---|---|---|---|
| Name | 44 | 87 | 93 | 429 | Alternative name |
| wt | L | R | A | S | — |
| mut 16 | M | | | | L44M |
| mut 17 | | K | | | R87K |
| mut 18 | | | G | | A93G |
| mut 19 | | | | E | S429E |
| mut 20 | M | K | | | L44M, R87K |
| mut 21 | M | | G | | L44M, A93G |
| mut 22 | M | | | E | L44M, S429E |
| mut 23 | | K | G | | R87K, A93G |

TABLE 5-continued

Mutation sites in ALPI with proposed amino acid changes

| | Position in mature ALPI | | | | |
|---|---|---|---|---|---|
| Name | 44 | 87 | 93 | 429 | Alternative name |
| mut 24 | | K | | E | R87K, S429E |
| mut 25 | | | G | E | A93G, S429E |
| mut 26 | M | K | G | | L44M, R87K, A93G |
| mut 27 | M | K | | E | L44M, R87K, S429E |
| mut 28 | M | | G | E | L44M, A93G, S429E |
| mut 29 | | K | G | E | R87K, A93G, S429E |
| mut 30 | M | K | G | E | L44M, R87K, A93G, S429E |

TABLE 6

Proposed double mutations in ALPP and ALPI within the vicinity of the active site
Additional mutants

| mut 31 | ALPP | S322G, R323V |
|---|---|---|
| mut 32 | ALPI | G322S, V323R |

TABLE 7 sALPI, but not sALPP and the chimer catALPI/crownALPP is $Zn^2$ dependent for retaining its specific activity in vitro.

| | T = 0 | T = 1½ h | T = 3 h | T = 22 h |
|---|---|---|---|---|
| sALPP | | | | |
| $0^a$ μM $Zn^{2+}$ | 122 | 103 | 105 | 100 |
| 10 μM $Zn^{2+}$ | 162 | 123 | 117 | 110 |
| 100 μM $Zn^{2+}$ | 131 | 128 | 150 | 132 |
| 1000 μM $Zn^{2+}$ | 126 | 135 | 125 | 114 |

TABLE 7-continued sALPI, but not sALPP and the chimer catALPI/crownALPP is
$Zn^2$ dependent for retaining its specific activity in vitro.

|  | T = 0 | T = 1½ h | T = 3 h | T = 22 h |
|---|---|---|---|---|
| sALPI |  |  |  |  |
| 0 μM $Zn^{2+}$ | 650 | 500 | 413 | 116 |
| 10 μM $Zn^{2+}$ | 717 | 648 | 953 | 746 |
| 100 μM $Zn^{2+}$ | 785 | 733 | 868 | 750 |
| 1000 μM $Zn^{2+}$ | 752 | 762 | 770 | 989 |
| catALPI/crownALPP |  |  |  |  |
| 0 μM $Zn^{2+}$ | 426 | 407 | 455 | 429 |
| 10 μM $Zn^{2+}$ | 443 | 500 | 479 | 462 |
| 100 μM $Zn^{2+}$ | 543 | 560 | 456 | 442 |
| 1000 μM $Zn^{2+}$ | 452 | 452 | 441 | 465 |

[a]No Zn-salt was added, however, the assay was performed in the presence of albumin (0.05%), which maybe a natural source of zinc; see result section.

TABLE 8

Specific activity of sALPI is decreased by more than 95% after
22 h at physiological (0.01 μM) $Zn^{2+}$ concentrations in the
absence of albumin, whereas sALPP and the chimer catALPI/
crownALPP retain more than 60, respectively 75% of their
initial specific activity under the same conditions.

|  | T = 0 | T = 1½ h | T = 3 h | T = 22 h |
|---|---|---|---|---|
| sALPP |  |  |  |  |
| 0 Zn + 100 mM EDTA | 29 | 0 | 0 | 0 |
| 0.01 μM $Zn^{2+}$ | 123 | 74 | 76 | 78 |
| 10 μM $Zn^{2+}$ | 131 | 94 | 88 | 92 |
| 1000 μM $Zn^{2+}$ | 118 | 6 | 6 | 3 |
| sALPI |  |  |  |  |
| 0 Zn + 100 mM EDTA | 290 | 4 | 10 | 0 |
| 0.01 μM $Zn^{2+}$ | 693 | 384 | 211 | 31 |
| 10 μM $Zn^{2+}$ | 785 | 541 | 386 | 324 |
| 1000 μM $Zn^{2+}$ | 737 | 505 | 382 | 232 |
| catALPI/crownALPP |  |  |  |  |
| 0 Zn + 100 mM EDTA | 161 | 8 | 5 | 0 |
| 0.01 μM $Zn^{2+}$ | 330 | 374 | 316 | 252 |
| 10 μM $Zn^{2+}$ | 543 | 386 | 315 | 266 |
| 1000 μM $Zn^{2+}$ | 531 | 306 | 299 | 196 |

TABLE 10

Unlimiting list of inflammatory diseases and organs affected

| Inflammation | Body part |
|---|---|
| Appendicitis | Appendix |
| Arteritis | Arteries |
| Arthritis | Joint |
| Blepharitis | Eyelids |
| Bronchiolitis | Bronchioles |
| Bronchitis | Bronchi |
| Bursitis | Bursa |
| Cervicitis | Cervix |
| Cholangitis | Bile duct |
| Cholecystitis | Gallbladder |
| Chorioamnionitis | Chorion and amnion (amniotic sac) |
| Colitis | Colon |
| Conjunctivitis | Conjunctiva |
| Cystitis | Bladder |
| Dacryoadenitis | Lacrimal gland |
| Dermatitis | Skin |
| Dermatomyositis | Skin and muscles |
| Encephalitis | Brain |
| Endocarditis | Endocardium |
| Endometritis | Endometrium |
| Enteritis | Small intestine |
| Enterocolitis | Small intestine and large intestine |
| Epicondylitis | Epicondyle |
| Epididymitis | Epididymis |
| Fasciitis | Fascia |
| Fibrositis | Fibrous connective tissue |
| Gastritis | Stomach |
| Gastroenteritis | Stomach and small intestine |
| Gingivitis | Gingiva |
| Glossitis | Tongue |
| Hepatitis | Liver |
| Hidradenitis suppurativa | Apocrine sweat glands |
| Ileitis | Ileum |
| Iritis | Iris |
| Laryngitis | Larynx |
| Mastitis | Mammary gland |
| Meningitis | Meninges |
| Myelitis | Spinal cord |
| Myocarditis | Myocardium |
| Myositis | Muscle |
| Nephritis | Kidney |
| Omphalitis | Umbilical cord |
| Oophoritis | Ovaries |
| Orchitis | Testicle |
| Osteitis | Bone |

TABLE 9

Dephosphorylating properties of different alkaline phosphatases towards the biological substrate ATP.

| standard Curve | | pNPP | BiAP | | sALPP | | sALPI | | catALPI/crownALPP | |
|---|---|---|---|---|---|---|---|---|---|---|
| ATP (μM) | LFI | units | LFI | ATP (μM) | LFI | ATP (μM) | LFI | ATP (μM) | LFI | ATP (μM) |
| 20.000 | 38845 | 0.5000 | 761 | 0.25 | 2273 | 1.01 | 213 | 0 | 530 | 0.13 |
| 10.000 | 20978 | 0.2500 | 390 | 0.06 | 7490 | 3.67 | 18 | 0 | 2366 | 1.06 |
| 5.000 | 10902 | 0.1250 | 1481 | 0.61 | 13633 | 6.79 | 24 | 0 | 7650 | 3.75 |
| 2.500 | 5714 | 0.0625 | 4893 | 2.35 | 21124 | 10.60 | 286 | 0.00 | 15642 | 7.81 |
| 1.250 | 2811 | 0.0313 | 11008 | 5.46 | 24450 | 12.29 | 707 | 0.22 | 22061 | 11.07 |
| 0.625 | 1422 | 0.0156 | 20401 | 10.23 | 31233 | 15.74 | 3762 | 1.77 | 30911 | 15.57 |
| 0.313 | 656 | 0.0078 | 24100 | 12.11 | 32382 | 16.32 | 9431 | 4.65 | 34178 | 17.23 |
| 0.156 | 342 | 0.0039 | 30479 | 15.35 | 37546 | 18.95 | 16197 | 8.09 | 37735 | 19.04 |
| 0.078 | 163 | 0.0020 | 36232 | 18.28 | 38418 | 19.39 | 22571 | 11.33 | 39841 | 20.11 |
| 0.039 | 80 | 0.0010 | 34902 | 17.60 | 40772 | 20.59 | 21065 | 10.57 | 40324 | 20.36 |
| 0.020 | 40 | 0.0005 | 39927 | 20.16 | 37848 | 19.10 | 34216 | 17.25 | 41683 | 21.05 |
| 0.000 | 4 | 0 | 41929 | 21.17 | 41299 | 20.85 | 41242 | 20.83 | 40177 | 20.28 | corr. coefficient = 0.9981 equation: y = 1967.1x + 275.9

TABLE 10-continued

Unlimiting list of inflammatory diseases and organs affected

| Inflammation | Body part |
|---|---|
| Otitis | Ear |
| Pancreatitis | Pancreas |
| Parotitis | Parotid gland |
| Pericarditis | Pericardium |
| Peritonitis | Peritoneum |
| Pharyngitis | Pharynx |
| Pleuritis | Pleura |
| Phlebitis | Veins |
| Pneumonitis | Lungs (also pneumonia) |
| Proctitis | Rectum |
| Prostatitis | Prostate |
| Pyelonephritis | Kidney |
| Rhinitis | Nasal lining |
| Salpingitis | Fallopian tubes |
| Sinusitis | Sinus of the skull |
| Stomatitis | Mouth |
| Synovitis | Synovial membrane |
| Tendinitis | Tendon |
| Tonsillitis | Tonsils |
| Uveitis | Uvea |
| Urethritis | Urethra |
| Vaginitis | Vaginal mucosa |
| Vasculitis | Blood vessels or lymph vessels |
| Vulvitis | Vulva |

The invention claimed is:

1. An alkaline phosphatase, wherein the alkaline phosphatase is isolated or recombinant and comprises:
   a human intestinal alkaline phosphatase (ALPI) wherein the crown domain of the human ALPI, corresponding to amino acids 366-430 of SEQ ID NO:2, is replaced with the crown domain of a human placental alkaline phosphatase (ALPP), corresponding to amino acids 366-430 of SEQ ID NO:1,
   wherein the alkaline phosphatase has dephosphorylation activity.

2. The alkaline phosphatase of claim 1, wherein the amino acid sequence of the alkaline phosphatase comprises a glycosylphosphatidylinositol ("GPI") signal sequence comprising a modification or a deletion in the GPI signal sequence and the modification or deletion results in the alkaline phosphatase being a secreted phosphatase.

3. A method for producing the alkaline phosphatase of claim 1, the method comprising:
   culturing a host cell comprising a polynucleotide encoding the alkaline phosphatase in a medium comprising Zn2+ and
   allowing the cell to produce the alkaline phosphatase.

4. The method according to claim 3, further comprising isolating the alkaline phosphatase.

5. The alkaline phosphatase of claim 1, produced by a method comprising:
   culturing a host cell comprising a polynucleotide encoding the alkaline phosphatase in a medium comprising Zn2+, and
   producing the alkaline phosphatase in the host cell.

6. An in vitro/biochemical method for dephosphorylating a substrate in an environment having a Zn2+ concentration lower than 10 uM, the method comprising:
utilizing the alkaline phosphatase of claim 1 to dephosphorylate the substrate.

7. The method according to claim 3, wherein the host cell is a mammalian cell.

8. The method according to claim 6, wherein the substrate is an adenosine phosphate.

9. The alkaline phosphatase of claim 1, wherein the crown domain of the human ALPP is as set forth by amino acids 366-430 of SEQ ID NO:1.

10. The alkaline phosphatase of claim 1, which comprises the amino acid sequence of SEQ ID NO:5.

11. The alkaline phosphatase of claim 1, wherein the alkaline phosphatase retains at least 75% of its initial specific activity at a $Zn^{2+}$ concentration of about 0.01 μM over a 22 hour period of time.

12. The alkaline phosphatase of claim 1, wherein the specific activity of the alkaline phosphatase is greater than secreted human placental alkaline phosphatase (sALPP), wherein the specific activity of the alkaline phosphatase and the human sALPP are tested at physiological $Zn^{2+}$ levels.

13. The alkaline phosphatase of claim 1, wherein the specific activity of the alkaline phosphatase is greater than the specific activity of secreted human ALPI, wherein the specific activity of the alkaline phosphatase and the human sALPI are tested at physiological $Zn^{2+}$ levels.

14. The alkaline phosphatase of claim 1, wherein the alkaline phosphatase has improved stability at 56° C. over a 22 hour period compared to human sALPP and sALPI.

15. The alkaline phosphatase of claim 1, wherein the alkaline phosphatase dephosphorylates an adenosine phosphate or para-nitrophenylphosphate (pNPP).

* * * * *

UNITED STATES PATENT AND TRADEMARK OFFICE
CERTIFICATE OF CORRECTION

| | | Page 1 of 1 |
|---|---|---|
| PATENT NO. | : 8,557,545 B2 | |
| APPLICATION NO. | : 12/451137 | |
| DATED | : October 15, 2013 | |
| INVENTOR(S) | : Velders et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 480 days.

Signed and Sealed this
Twenty-first Day of April, 2015

Michelle K. Lee
*Director of the United States Patent and Trademark Office*

```
                        SEQUENCE LISTING

<160> NUMBER OF SEQ ID NOS: 6

<210> SEQ ID NO 1
<211> LENGTH: 513
<212> TYPE: PRT
<213> ORGANISM: Homo sapiens
<220> FEATURE:
<221> NAME/KEY: DOMAIN
<222> LOCATION: (366)..(430)

<400> SEQUENCE: 1

Ile Ile Pro Val Glu Glu Asn Pro Asp Phe Trp Asn Arg Glu Ala
1               5                   10                  15

Ala Glu Ala Leu Gly Ala Ala Lys Lys Leu Gln Pro Ala Gln Thr Ala
            20                  25                  30

Ala Lys Asn Leu Ile Ile Phe Leu Gly Asp Gly Met Gly Val Ser Thr
        35                  40                  45

Val Thr Ala Ala Arg Ile Leu Lys Gly Gln Lys Lys Asp Lys Leu Gly
    50                  55                  60

Pro Glu Ile Pro Leu Ala Met Asp Arg Phe Pro Tyr Val Ala Leu Ser
65                  70                  75                  80

Lys Thr Tyr Asn Val Asp Lys His Val Pro Asp Ser Gly Ala Thr Ala
                85                  90                  95

Thr Ala Tyr Leu Cys Gly Val Lys Gly Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Lys Ala Gly Lys Ser Val Gly
    130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Val Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Arg Met Gly Thr Pro Asp Pro Glu Tyr Pro Asp Asp Tyr Ser Gln Gly
    210                 215                 220

Gly Thr Arg Leu Asp Gly Lys Asn Leu Val Gln Glu Trp Leu Ala Lys
```

```
                    225                 230                 235                 240

Arg Gln Gly Ala Arg Tyr Val Trp Asn Arg Thr Glu Leu Met Gln Ala
                            245                 250                 255

Ser Leu Asp Pro Ser Val Thr His Leu Met Gly Leu Phe Glu Pro Gly
                            260                 265                 270

Asp Met Lys Tyr Glu Ile His Arg Asp Ser Thr Leu Asp Pro Ser Leu
                            275                 280                 285

Met Glu Met Thr Glu Ala Ala Leu Arg Leu Leu Ser Arg Asn Pro Arg
                    290                 295                 300

Gly Phe Phe Leu Phe Val Glu Gly Gly Arg Ile Asp His Gly His His
            305                 310                 315                 320

Glu Ser Arg Ala Tyr Arg Ala Leu Thr Glu Thr Ile Met Phe Asp Asp
                            325                 330                 335

Ala Ile Glu Arg Ala Gly Gln Leu Thr Ser Glu Asp Thr Leu Ser
                            340                 345                 350

Leu Val Thr Ala Asp His Ser His Val Phe Ser Phe Gly Gly Tyr Pro
                    355                 360                 365

Leu Arg Gly Ser Ser Ile Phe Gly Leu Ala Pro Gly Lys Ala Arg Asp
                    370                 375                 380

Arg Lys Ala Tyr Thr Val Leu Leu Tyr Gly Asn Gly Pro Gly Tyr Val
            385                 390                 395                 400

Leu Lys Asp Gly Ala Arg Pro Asp Val Thr Glu Ser Glu Ser Gly Ser
                            405                 410                 415

Pro Glu Tyr Arg Gln Gln Ser Ala Val Pro Leu Asp Glu Glu Thr His
                            420                 425                 430

Ala Gly Glu Asp Val Ala Val Phe Ala Arg Gly Pro Gln Ala His Leu
                            435                 440                 445

Val His Gly Val Gln Glu Gln Thr Phe Ile Ala His Val Met Ala Phe
                    450                 455                 460

Ala Ala Cys Leu Glu Pro Tyr Thr Ala Cys Asp Leu Ala Pro Pro Ala
            465                 470                 475                 480

Gly Thr Thr Asp Ala Ala His Pro Gly Arg Ser Val Val Pro Ala Leu
                            485                 490                 495

Leu Pro Leu Leu Ala Gly Thr Leu Leu Leu Glu Thr Ala Thr Ala
                            500                 505                 510

Pro

<210> SEQ ID NO 2
<211> LENGTH: 509
<212> TYPE: PRT
<213> ORGANISM: Homo sapiens
<220> FEATURE:
<221> NAME/KEY: DOMAIN
<222> LOCATION: (366)..(430)

<400> SEQUENCE: 2

Val Ile Pro Ala Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
                20                  25                  30

Ala Lys Asn Leu Ile Leu Phe Leu Gly Asp Gly Leu Gly Val Pro Thr
                35                  40                  45

Val Thr Ala Thr Arg Ile Leu Lys Gly Gln Lys Asn Gly Lys Leu Gly
        50                  55                  60

Pro Glu Thr Pro Leu Ala Met Asp Arg Phe Pro Tyr Leu Ala Leu Ser
65                  70                  75                  80
```

```
Lys Thr Tyr Asn Val Asp Arg Gln Val Pro Asp Ser Ala Ala Thr Ala
                85                  90                  95

Thr Ala Tyr Leu Cys Gly Val Lys Ala Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Gln Ala Gly Lys Ser Val Gly
130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Pro Met Gly Thr Pro Asp Pro Glu Tyr Pro Ala Asp Ala Ser Gln Asn
    210                 215                 220

Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
                245                 250                 255

Ser Leu Asp Gln Ser Val Thr His Leu Met Gly Leu Phe Glu Pro Gly
            260                 265                 270

Asp Thr Lys Tyr Glu Ile His Arg Asp Pro Thr Leu Asp Pro Ser Leu
        275                 280                 285

Met Glu Met Thr Glu Ala Ala Leu Arg Leu Leu Ser Arg Asn Pro Arg
    290                 295                 300

Gly Phe Tyr Leu Phe Val Glu Gly Gly Arg Ile Asp His Gly His His
305                 310                 315                 320

Glu Gly Val Ala Tyr Gln Ala Leu Thr Glu Ala Val Met Phe Asp Asp
                325                 330                 335

Ala Ile Glu Arg Ala Gly Gln Leu Thr Ser Glu Glu Asp Thr Leu Thr
            340                 345                 350

Leu Val Thr Ala Asp His Ser His Val Phe Ser Phe Gly Gly Tyr Thr
        355                 360                 365

Leu Arg Gly Ser Ser Ile Phe Gly Leu Ala Pro Ser Lys Ala Gln Asp
    370                 375                 380

Ser Lys Ala Tyr Thr Ser Ile Leu Tyr Gly Asn Gly Pro Gly Tyr Val
385                 390                 395                 400

Phe Asn Ser Gly Val Arg Pro Asp Val Asn Glu Ser Glu Ser Gly Ser
                405                 410                 415

Pro Asp Tyr Gln Gln Gln Ala Val Pro Leu Ser Ser Glu Thr His
            420                 425                 430

Gly Gly Glu Asp Val Ala Val Phe Ala Arg Gly Pro Gln Ala His Leu
        435                 440                 445

Val His Gly Val Gln Glu Gln Ser Phe Val Ala His Val Met Ala Phe
    450                 455                 460

Ala Ala Cys Leu Glu Pro Tyr Thr Ala Cys Asp Leu Ala Pro Pro Ala
465                 470                 475                 480

Cys Thr Thr Asp Ala Ala His Pro Val Ala Ser Leu Pro Leu Leu
                485                 490                 495

Ala Gly Thr Leu Leu Leu Leu Gly Ala Ser Ala Ala Pro
```

```
              500             505

<210> SEQ ID NO 3
<211> LENGTH: 513
<212> TYPE: PRT
<213> ORGANISM: Homo sapiens
<220> FEATURE:
<221> NAME/KEY: DOMAIN
<222> LOCATION: (366)..(430)

<400> SEQUENCE: 3

Ile Ile Pro Val Glu Glu Asn Pro Asp Phe Trp Asn Arg Gln Ala
1               5                   10                  15

Ala Glu Ala Leu Gly Ala Ala Lys Lys Leu Gln Pro Ala Gln Thr Ala
            20                  25                  30

Ala Lys Asn Leu Ile Ile Phe Leu Gly Asp Gly Met Gly Val Ser Thr
        35                  40                  45

Val Thr Ala Ala Arg Ile Leu Lys Gly Gln Lys Lys Asp Lys Leu Gly
50                  55                  60

Pro Glu Thr Phe Leu Ala Met Asp Arg Phe Pro Tyr Val Ala Leu Ser
65                  70                  75                  80

Lys Thr Tyr Ser Val Asp Lys His Val Pro Asp Ser Gly Ala Thr Ala
                85                  90                  95

Thr Ala Tyr Leu Cys Gly Val Lys Gly Asn Phe Gln Thr Ile Gly Leu
            100                 105                 110

Ser Ala Ala Arg Phe Asn Gln Cys Asn Thr Thr Arg Gly Asn Glu
            115                 120                 125

Val Ile Ser Val Met Asn Arg Ala Lys Lys Ala Gly Lys Ser Val Gly
    130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Val Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Pro Met Gly Thr Pro Asp Pro Glu Tyr Pro Asp Asp Tyr Ser Gln Gly
    210                 215                 220

Gly Thr Arg Leu Asp Gly Lys Asn Leu Val Gln Glu Trp Leu Ala Lys
225                 230                 235                 240

His Gln Gly Ala Arg Tyr Val Trp Asn Arg Thr Glu Leu Leu Gln Ala
                245                 250                 255

Ser Leu Asp Pro Ser Val Thr His Leu Met Gly Leu Phe Glu Pro Gly
            260                 265                 270

Asp Met Lys Tyr Glu Ile His Arg Asp Ser Thr Leu Asp Pro Ser Leu
        275                 280                 285

Met Glu Met Thr Glu Ala Ala Leu Leu Leu Leu Ser Arg Asn Pro Arg
    290                 295                 300

Gly Phe Phe Leu Phe Val Glu Gly Gly Arg Ile Asp His Gly His His
305                 310                 315                 320

Glu Ser Arg Ala Tyr Arg Ala Leu Thr Glu Thr Ile Met Phe Asp Asp
                325                 330                 335

Ala Ile Glu Arg Ala Gly Gln Leu Thr Ser Glu Glu Asp Thr Leu Ser
            340                 345                 350

Leu Val Thr Ala Asp His Ser His Val Phe Ser Phe Gly Gly Tyr Pro
```

```
                     355                 360                 365
Leu Arg Gly Ser Ser Ile Phe Gly Leu Ala Pro Gly Lys Ala Arg Asp
370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
                405                 410                 415

Pro Glu Tyr Arg Gln Gln Ser Ala Val Pro Leu Asp Gly Glu Thr His
            420                 425                 430

Ala Gly Glu Asp Val Ala Val Phe Ala Arg Gly Pro Gln Ala His Leu
        435                 440                 445

Val His Gly Val Gln Glu Gln Thr Phe Ile Ala His Val Met Ala Phe
450                 455                 460

Ala Ala Cys Leu Glu Pro Tyr Thr Ala Cys Asp Leu Ala Pro Arg Ala
465                 470                 475                 480

Gly Thr Thr Asp Ala Ala His Pro Gly Pro Ser Val Val Pro Ala Leu
                485                 490                 495

Leu Pro Leu Leu Ala Gly Thr Leu Leu Leu Gly Thr Ala Thr Ala
            500                 505                 510
Pro

<210> SEQ ID NO 4
<211> LENGTH: 507
<212> TYPE: PRT
<213> ORGANISM: Homo sapiens
<220> FEATURE:
<221> NAME/KEY: DOMAIN
<222> LOCATION: (370)..(434)

<400> SEQUENCE: 4

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
                20                  25                  30

Val Ala Lys Asn Val Ile Met Phe Leu Gly Asp Gly Met Gly Val Ser
            35                  40                  45

Thr Val Thr Ala Ala Arg Ile Leu Lys Gly Gln Leu His His Asn Pro
50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205
```

```
Met Tyr Pro Lys Asn Lys Thr Asp Val Glu Tyr Ser Asp Glu Lys
    210                 215                 220

Ala Arg Gly Thr Arg Leu Asp Gly Leu Asp Leu Val Asp Thr Trp Lys
225                 230                 235                 240

Ser Phe Lys Pro Arg His Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Ala Ile Gln Ile Leu Arg
290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
        435                 440                 445

Pro Met Ala His Leu Leu His Gly Val His Glu Gln Asn Tyr Val Pro
450                 455                 460

His Val Met Ala Tyr Ala Ala Cys Ile Gly Ala Asn Leu Gly His Cys
465                 470                 475                 480

Ala Pro Ala Ser Ser Ala Gly Ser Leu Ala Ala Gly Pro Leu Leu Leu
                485                 490                 495

Ala Leu Ala Leu Tyr Pro Leu Ser Val Leu Phe
            500                 505

<210> SEQ ID NO 5
<211> LENGTH: 484
<212> TYPE: PRT
<213> ORGANISM: Homo sapiens
<220> FEATURE:
<221> NAME/KEY: DOMAIN
<222> LOCATION: (366)..(430)

<400> SEQUENCE: 5

Val Ile Pro Ala Glu Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
            20                  25                  30

Ala Lys Asn Leu Ile Leu Phe Leu Gly Asp Gly Leu Gly Val Pro Thr
        35                  40                  45

Val Thr Ala Thr Arg Ile Leu Lys Gly Gln Lys Asn Gly Lys Leu Gly
50                  55                  60
```

```
Pro Glu Thr Pro Leu Ala Met Asp Arg Phe Pro Tyr Leu Ala Leu Ser
 65                  70                  75                  80

Lys Thr Tyr Asn Val Asp Arg Gln Val Pro Asp Ser Ala Ala Thr Ala
                 85                  90                  95

Thr Ala Tyr Leu Cys Gly Val Lys Ala Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Gln Ala Gly Lys Ser Val Gly
    130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Pro Met Gly Thr Pro Asp Pro Glu Tyr Pro Ala Asp Ala Ser Gln Asn
210                 215                 220

Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
                245                 250                 255

Ser Leu Asp Gln Ser Val Thr His Leu Met Gly Leu Phe Glu Pro Gly
            260                 265                 270

Asp Thr Lys Tyr Glu Ile His Arg Asp Pro Thr Leu Asp Pro Ser Leu
        275                 280                 285

Met Glu Met Thr Glu Ala Ala Leu Arg Leu Ser Arg Asn Pro Arg
    290                 295                 300

Gly Phe Tyr Leu Phe Val Glu Gly Gly Arg Ile Asp His Gly His His
305                 310                 315                 320

Glu Gly Val Ala Tyr Gln Ala Leu Thr Glu Ala Val Met Phe Asp Asp
                325                 330                 335

Ala Ile Glu Arg Ala Gly Gln Leu Thr Ser Glu Glu Asp Thr Leu Thr
            340                 345                 350

Leu Val Thr Ala Asp His Ser His Val Phe Ser Phe Gly Gly Tyr Pro
        355                 360                 365

Leu Arg Gly Ser Ser Ile Phe Gly Leu Ala Pro Gly Lys Ala Arg Asp
    370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
                405                 410                 415

Pro Glu Tyr Arg Gln Gln Ser Ala Val Pro Leu Asp Glu Glu Thr His
            420                 425                 430

Gly Gly Glu Asp Val Ala Val Phe Ala Arg Gly Pro Gln Ala His Leu
        435                 440                 445

Val His Gly Val Gln Glu Gln Ser Phe Val Ala His Val Met Ala Phe
    450                 455                 460

Ala Ala Cys Leu Glu Pro Tyr Thr Ala Cys Asp Leu Ala Pro Pro Ala
465                 470                 475                 480

Cys Thr Thr Asp
```

```
<210> SEQ ID NO 6
<211> LENGTH: 484
<212> TYPE: PRT
<213> ORGANISM: Homo sapiens
<220> FEATURE:
<221> NAME/KEY: DOMAIN
<222> LOCATION: (366)..(430)

<400> SEQUENCE: 6
```

Ile Ile Pro Val Glu Glu Asn Pro Asp Phe Trp Asn Arg Glu Ala
1               5                   10                  15

Ala Glu Ala Leu Gly Ala Ala Lys Lys Leu Gln Pro Ala Gln Thr Ala
            20                  25                  30

Ala Lys Asn Leu Ile Ile Phe Leu Gly Asp Gly Met Gly Val Ser Thr
        35                  40                  45

Val Thr Ala Ala Arg Ile Leu Lys Gly Gln Lys Lys Asp Lys Leu Gly
50                  55                  60

Pro Glu Ile Pro Leu Ala Met Asp Arg Phe Pro Tyr Val Ala Leu Ser
65                  70                  75                  80

Lys Thr Tyr Asn Val Asp Lys His Val Pro Asp Ser Gly Ala Thr Ala
                85                  90                  95

Thr Ala Tyr Leu Cys Gly Val Lys Gly Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Lys Ala Gly Lys Ser Val Gly
130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Val Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Arg Met Gly Thr Pro Asp Pro Glu Tyr Pro Asp Asp Tyr Ser Gln Gly
210                 215                 220

Gly Thr Arg Leu Asp Gly Lys Asn Leu Val Gln Glu Trp Leu Ala Lys
225                 230                 235                 240

Arg Gln Gly Ala Arg Tyr Val Trp Asn Arg Thr Glu Leu Met Gln Ala
                245                 250                 255

Ser Leu Asp Pro Ser Val Thr His Leu Met Gly Leu Phe Glu Pro Gly
            260                 265                 270

Asp Met Lys Tyr Glu Ile His Arg Asp Ser Thr Leu Asp Pro Ser Leu
        275                 280                 285

Met Glu Met Thr Glu Ala Ala Leu Arg Leu Leu Ser Arg Asn Pro Arg
290                 295                 300

Gly Phe Phe Leu Phe Val Glu Gly Gly Arg Ile Asp His Gly His His
305                 310                 315                 320

Glu Ser Arg Ala Tyr Arg Ala Leu Thr Glu Thr Ile Met Phe Asp Asp
                325                 330                 335

Ala Ile Glu Arg Ala Gly Gln Leu Thr Ser Glu Glu Asp Thr Leu Ser
            340                 345                 350

Leu Val Thr Ala Asp His Ser His Val Phe Ser Phe Gly Gly Tyr Thr
        355                 360                 365

-continued

```
Leu Arg Gly Ser Ser Ile Phe Gly Leu Ala Pro Ser Lys Ala Gln Asp
    370                 375                 380

Ser Lys Ala Tyr Thr Ser Ile Leu Tyr Gly Asn Gly Pro Gly Tyr Val
385                 390                 395                 400

Phe Asn Ser Gly Val Arg Pro Asp Val Asn Glu Ser Glu Ser Gly Ser
                405                 410                 415

Pro Asp Tyr Gln Gln Gln Ala Ala Val Pro Leu Ser Ser Glu Thr His
            420                 425                 430

Ala Gly Glu Asp Val Ala Val Phe Ala Arg Gly Pro Gln Ala His Leu
        435                 440                 445

Val His Gly Val Gln Glu Gln Thr Phe Ile Ala His Val Met Ala Phe
    450                 455                 460

Ala Ala Cys Leu Glu Pro Tyr Thr Ala Cys Asp Leu Ala Pro Pro Ala
465                 470                 475                 480

Gly Thr Thr Asp
```